(12) United States Patent
Ott et al.

(10) Patent No.: US 8,332,233 B2
(45) Date of Patent: Dec. 11, 2012

(54) METHOD AND SYSTEM FOR COLLECTING AND ANALYZING HOLTER DATA EMPLOYING A WEB SITE

(75) Inventors: James E. Ott, Kirkwood, MO (US);
Steven M. Kidder, Oak Creek, WI (US)

(73) Assignee: Biomedical Systems Corporation, St. Louis, MO (US)

( * ) Notice: Subject to any disclaimer, the term of this patent is extended or adjusted under 35 U.S.C. 154(b) by 1539 days.

(21) Appl. No.: 11/023,263

(22) Filed: Dec. 27, 2004

(65) Prior Publication Data
US 2005/0108055 A1 May 19, 2005

Related U.S. Application Data

(63) Continuation-in-part of application No. 10/294,541, filed on Nov. 13, 2002, now Pat. No. 7,353,179.

(60) Provisional application No. 60/614,154, filed on Sep. 29, 2004.

(51) Int. Cl.
*G06Q 10/00* (2012.01)
(52) U.S. Cl. .......................................................... 705/2
(58) Field of Classification Search ........................ 705/2
See application file for complete search history.

(56) References Cited

U.S. PATENT DOCUMENTS

| | | | |
|---|---|---|---|
| 5,305,202 A * | 4/1994 | Gallant et al. | 600/524 |
| 5,339,821 A | 8/1994 | Fujimoto | |
| 5,544,649 A | 8/1996 | David et al. | |
| 5,544,661 A | 8/1996 | Davis et al. | |
| 5,623,935 A * | 4/1997 | Faisandier | 600/509 |
| 5,669,391 A * | 9/1997 | Williams | 600/510 |
| 5,701,894 A * | 12/1997 | Cherry et al. | 600/300 |
| 5,944,659 A | 8/1999 | Flach et al. | |
| 5,987,519 A | 11/1999 | Peifer et al. | |
| 5,997,476 A | 12/1999 | Brown | |
| 6,024,699 A | 2/2000 | Surwit et al. | |
| 6,039,688 A | 3/2000 | Douglas et al. | |
| 6,064,906 A | 5/2000 | Langberg et al. | |
| 6,101,478 A | 8/2000 | Brown | |
| 6,108,800 A | 8/2000 | Asawa | |
| 6,176,826 B1 | 1/2001 | Shimura et al. | |
| 6,283,761 B1 | 9/2001 | Joao | |
| 6,302,844 B1 * | 10/2001 | Walker et al. | 600/300 |
| 6,327,594 B1 | 12/2001 | Van Huben et al. | |
| 6,364,834 B1 | 4/2002 | Reuss et al. | |
| 6,416,471 B1 * | 7/2002 | Kumar et al. | 600/300 |
| 6,561,975 B1 | 5/2003 | Pool et al. | |
| 6,579,242 B2 | 6/2003 | Bui et al. | |
| 6,602,191 B2 | 8/2003 | Quy | |
| 6,622,045 B2 * | 9/2003 | Snell et al. | 607/30 |
| 6,681,003 B2 * | 1/2004 | Linder et al. | 379/106.02 |
| 6,701,184 B2 | 3/2004 | Henkin | |

(Continued)

*Primary Examiner* — Hiep V Nguyen
(74) *Attorney, Agent, or Firm* — Senniger Powers LLP

(57) ABSTRACT

A central server controls the receipt and analysis of patient medical data and patient information. The central server receives patient medical data and patient information from a sensor or a remote computer. A storage system of the central server stores the received patient medical data, patient information, and the associated medical report prepared by the analysis software on the central server after analysis of the patient medical data. The medical report associated with the patient medical data is transmitted from the central server to the remote computer. Also, a method controls the acquisition and analysis of patient medical data over a network by a central server from a remote computer operably interconnected by the network with the central server.

39 Claims, 16 Drawing Sheets

U.S. PATENT DOCUMENTS

| | | |
|---|---|---|
| 6,708,057 B2 | 3/2004 | Morganroth |
| 6,749,566 B2 | 6/2004 | Russ |
| 6,820,057 B1 * | 11/2004 | Loch et al. .................. 705/2 |
| 2001/0007053 A1 | 7/2001 | Bardy |
| 2001/0044588 A1 | 11/2001 | Mault |
| 2001/0051881 A1 | 12/2001 | Filler |
| 2002/0013716 A1 | 1/2002 | Dunham et al. |
| 2002/0016719 A1 | 2/2002 | Nemeth et al. |
| 2002/0019745 A1 | 2/2002 | Yamigiwa et al. |
| 2002/0035336 A1 | 3/2002 | Henkin |
| 2002/0046047 A1 | 4/2002 | Budd |
| 2002/0082867 A1 | 6/2002 | MacCarter et al. |
| 2002/0143372 A1 | 10/2002 | Snell et al. |
| 2002/0181680 A1 | 12/2002 | Linder et al. |
| 2002/0183599 A1 | 12/2002 | Castellanos |
| 2002/0184055 A1 | 12/2002 | Naghavi et al. |
| 2002/0198473 A1 | 12/2002 | Kumar et al. |
| 2003/0028442 A1 | 2/2003 | Wagstaff et al. |
| 2003/0032991 A1 | 2/2003 | Poore |
| 2003/0045787 A1 | 3/2003 | Schulze et al. |
| 2003/0097075 A1 * | 5/2003 | Kuo .............................. 600/500 |
| 2003/0200114 A1 | 10/2003 | Ogino et al. |
| 2004/0025030 A1 | 2/2004 | Corbett-Clark et al. |
| 2004/0039264 A1 | 2/2004 | Bardy |
| 2004/0088027 A1 | 5/2004 | Burnes et al. |
| 2004/0088374 A1 | 5/2004 | Webb et al. |
| 2004/0093239 A1 | 5/2004 | Ott et al. |
| 2005/0177400 A1 | 8/2005 | Rosenfeld et al. |

* cited by examiner

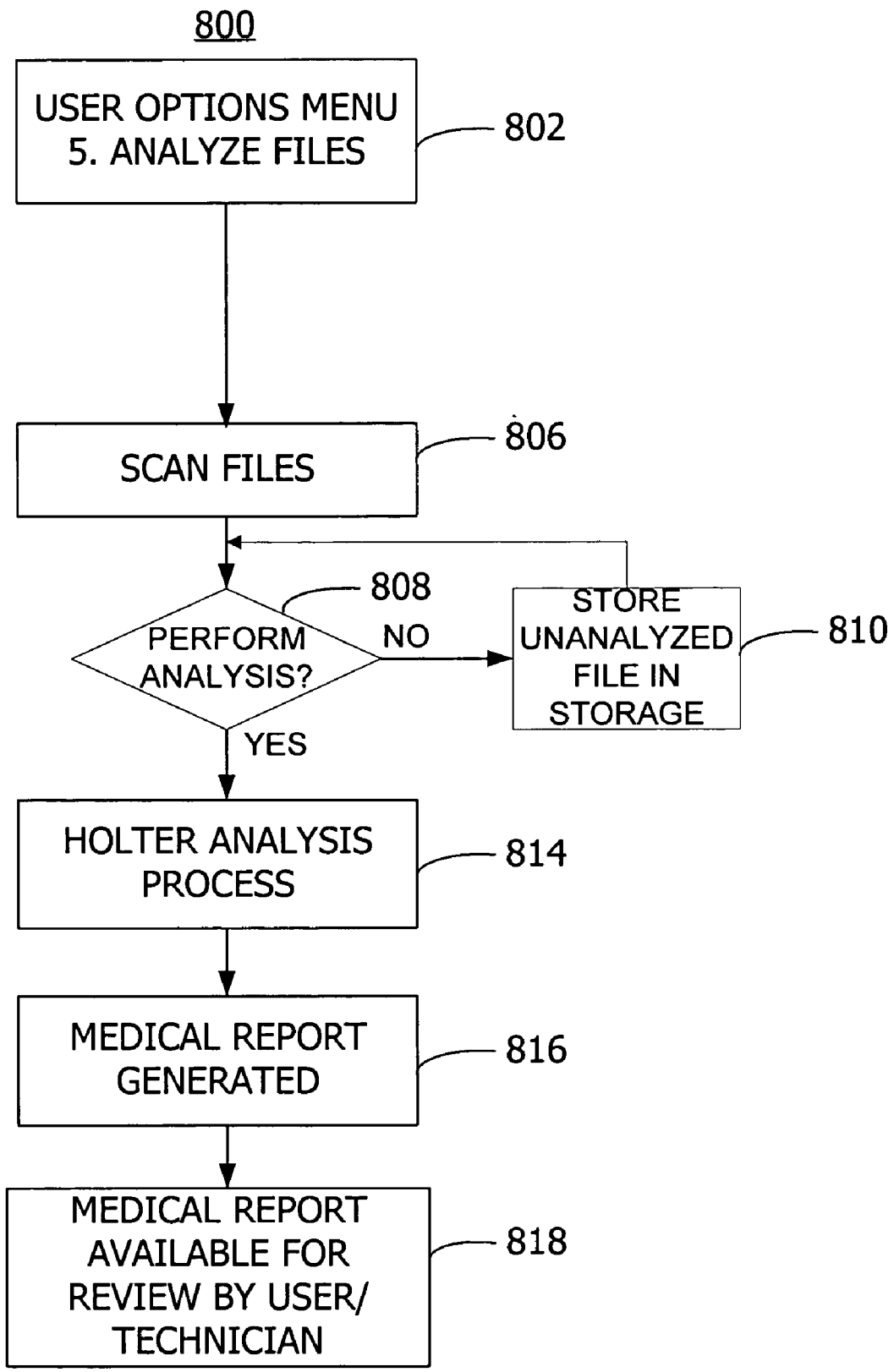

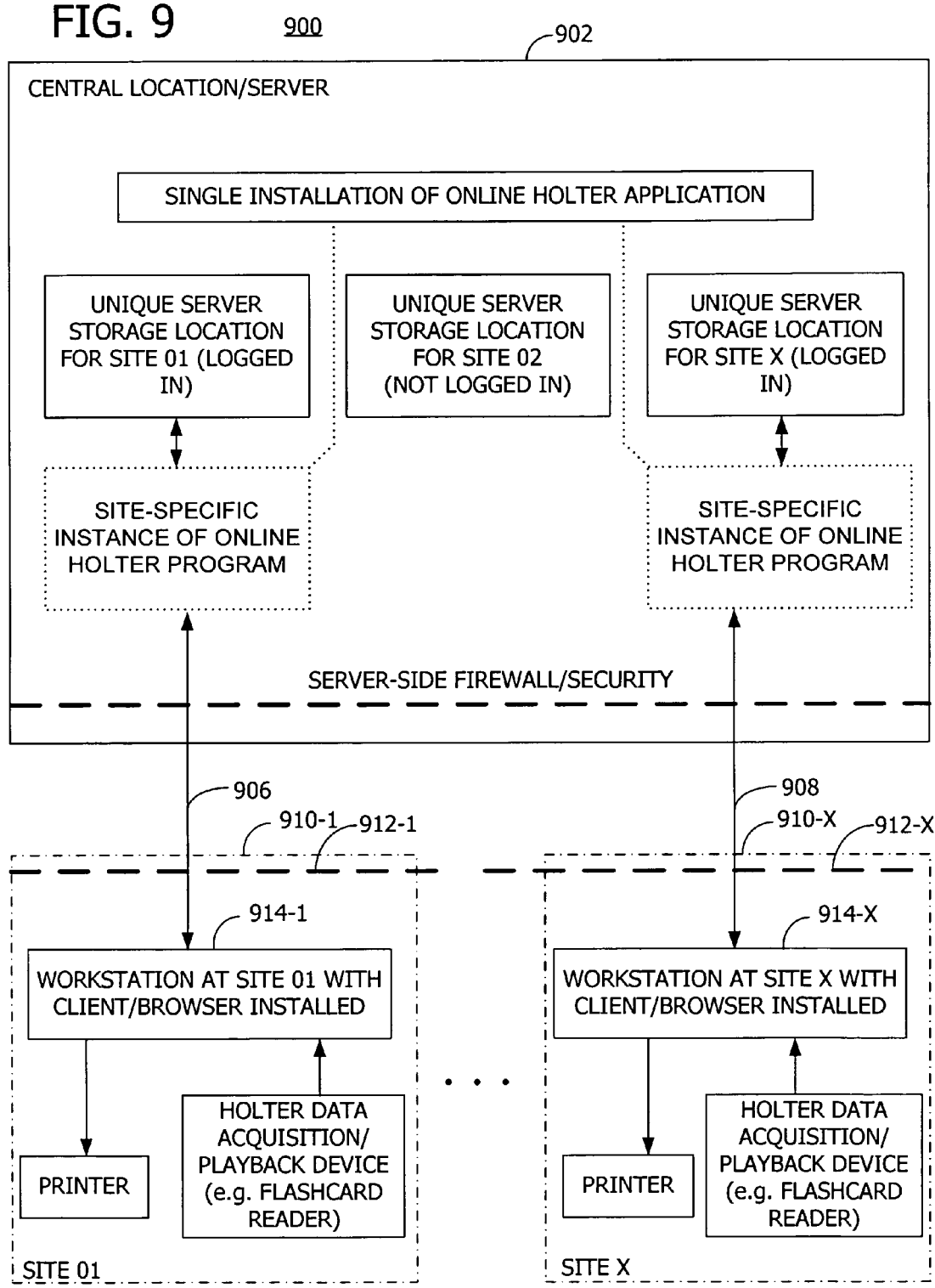

METHOD AND SYSTEM FOR COLLECTING AND ANALYZING HOLTER DATA EMPLOYING A WEB SITE

CROSS REFERENCE TO RELATED APPLICATION

The present application claims the benefit of U.S. Provisional patent application Ser. No. 10/614,154, filed on Sep. 29, 2004 and is a continuation-in-part of U.S. patent application Ser. No. 10/294,541, filed on Nov. 13, 2002, entitled "SYSTEM AND METHOD FOR HANDLING THE ACQUISITION AND ANALYSIS OF MEDICAL DATA OVER A NETWORK," which are incorporated herein by reference.

FIELD OF THE INVENTION

The invention relates generally to a system and method for handling medical data on a network. In particular, the invention includes uploading patient medical data and patient information to a central server for analyzing the patient medical data and preparing a medical report associated with the patient medical data.

BACKGROUND OF THE INVENTION

Medical devices such as medical sensors are used both in medical institutions and at home to monitor one or more vital signs or to observe and record patient medical data. The medical data is transported to medical personnel who are often specialists and have the expertise to analyze the medical data and to prepare a medical report associated with the medical data. In some instances, the medical personnel use specialized systems, methods, test systems, expert workstations and/or software to aid in the analysis of the patient medical data and in the preparation of a medical report which analyzes the patient medical data.

To accomplish this, the medical data must be readily available to the medical specialists. However, often the patient and medical data are located in remote locations away from the location of an available medical specialist. One solution is for the medical specialist to travel to the remote location such as a remote medical facility, hospital, or doctor's office to gain access to the patient medical data and to analyze the report. In other cases, the medical data is obtained at the remote facility and shipped via mail or courier service to medical facility or medical specialist located at a remote location. However, these processes are both costly and time consuming and are not desirable when the timely analysis of the patient medical data is critical to providing timely medical care to patients who may have a severe or life threatening condition.

Additionally, there are systems for remotely monitoring medical data from a patient by a medical care provider. In one such system, U.S. Pat. No. 5,339,821, issued to Fujimoto, a home medical system allows any patient to measure his or her daily condition at home and undergo a check or an inquiry diagnosis by a medical specialist or doctor located at a remote medical facility. Other systems such as U.S. Pat. No. 5,544,649, issued to David et al., provide an interactive remote patient monitoring system. However, these direct transactions often are unreliable due to the insecure nature of the transmission, the large amount of data required to be transmitted, and/or the need to associate patient information with the patient medical data and subsequently with the medical report associated with the patient medical data. Furthermore, these systems are administratively challenging and do not provide for control and management of the access to and the analysis of the patient medical data by medical specialists.

Therefore, it is desirable to have a system and method of sensing and acquiring patient medical data at a remote location for analysis by a medical specialist who is located at a remote distance. Such a system would control access to the patient medical data by the medical specialist who performs medical analysis of the patient medical data. Based on the patient medical data, the medical specialist working at an analysis workstation prepares a medical report associated with the patient medical data. The medical report is selectively provided to the remote location for review and access by local medical personnel or by the patient.

It is also desirable to have a system and method of sensing and acquiring patient medical data at a remote location for analysis through a web site hosted by a central server. Such system would provide analysis of the patient medical data using analysis software on the central server. The central server stores a medical report based on the analyzed medical data on the central server. The medical report is accessible to the patient and/or local medical personnel through the web site.

BRIEF DESCRIPTION OF THE INVENTION

In one embodiment, the invention is a method of analyzing ECG data of a patient at a site remote from the patient. The ECG data is sensed from the patient. The sensed ECG data is transferred to a central server over a communication network. The transferred ECG data is stored in a data storage area of the central server. The stored ECG data is analyzed on the central server using analysis software available via the central server to generate a report on the central server. The report is received from the central server.

In accordance with another embodiment, the invention is a method for analyzing ECG data of a patient over a network. A connection is established between a server and a device having access to the ECG data of the patient. The ECG data is stored in a data storage area of the server. The stored ECG data is analyzed on the server to generate a report on the server. The report related to the analyzed ECG data is transmitted from the server to the device.

According to another embodiment, a system permits a user to collect and analyze ECG data of a patient. A sensor senses the ECG data from a patient. A first interface transfers the sensed ECG data to a computer. A second interface transfers the sensed ECG data from the computer to a central server over a communication network so that the ECG data is stored on the central server. A third interface for use by the user analyzes the stored ECG data using analysis software available on the central server to generate a report on the central server. A fourth interface transfers the report to the computer.

According to yet another embodiment, a system analyzes ECG data of a patient over a network. An interface receives ECG data from a source to the central server over a communication network. A storage area stores the received ECG data. An analysis software analyzes the stored ECG data. A processor analyzes the stored ECG data using the analysis software to generate a report on the server. The interface also transfers the report from the central server to the source.

The system and method of the present invention has a number of advantages over the prior art. The present system provides for remote acquisition of patient medical data and patient information at a local easily accessible medical facility or possibly at home. The patient medical data and patient information is transmitted to a central server that controls the receipt of and access to the patient medical data. The patient medical data is analyzed on the central server using the analysis software on the central server. Access to the medical reports are controlled by the central server and provided to the remote computer at the remote location for receipt and review by the local medical provider or the patient. Such a system provides a secure, timely and efficient acquisition and analysis of patient medical data that is not provided by prior art systems.

Other aspects and forms of the invention will be in part apparent and in part pointed out hereinafter.

BRIEF DESCRIPTION OF THE DRAWINGS

FIG. 8 is a block diagram illustrating a method of analyzing patient medical data using the analysis software on a central server and creating a medical report associated with the patient medical data according to one embodiment of the invention.

FIG. 9 is a block diagram illustrating users accessing the central server for analyzing patients' medical data for patients according to one embodiment of the invention.

Corresponding reference characters and designations generally indicate corresponding parts throughout the drawings.

DETAILED DESCRIPTION

Figure 1:
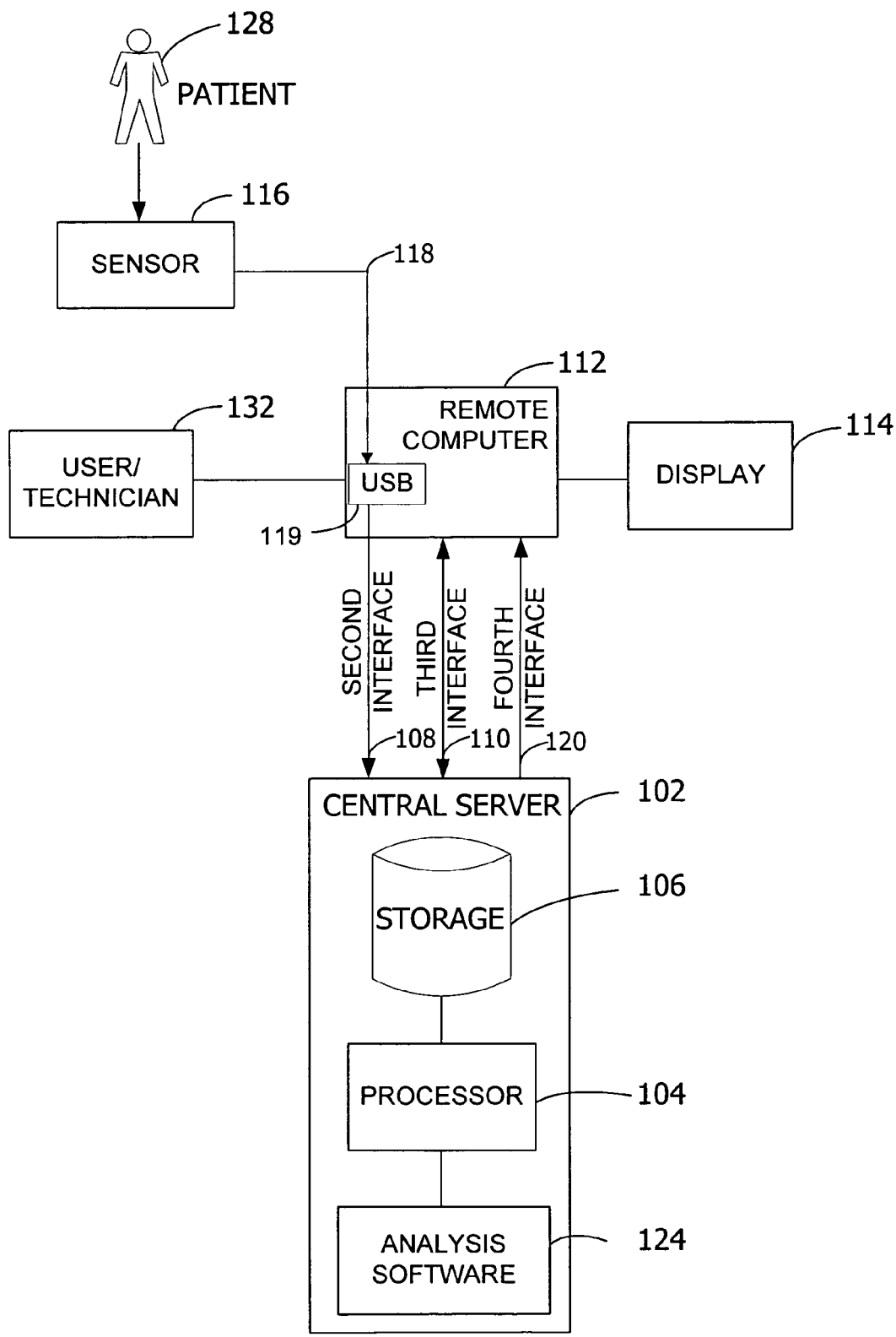
FIG. 1 is a diagram illustrating a system for analyzing patient medical data over a network according to one embodiment of the invention.

Referring now to FIG. 1, a block diagram illustrates one preferred embodiment of a system 100 for handling the acquisition and analysis of patient medical data and patient information over a network. Patient information is specific data such as name, address, contact information, patient medical history, medical care provider information, medical insurance data, and/or other information associated with a patient 128. Patient medical data is medical data associated with one or more body functions of the patient 128 that have been measured and recorded, such as ECG data, AECG data, Holter data, or the like. The system 100 includes a central server 102 with a processor 104, a storage 106, and analysis software 124. The processor 104 is configured to associate the patient medical data with the patient information. The storage 106 may be any storage system such as local memory, fixed storage disks, remote storage disks, a database, or otherwise configured to store patient medical data, patient information and/or medical reports. The analysis software 124 may be medical data analysis software, such as ECG analysis software configured to scan raw ECG data from an ECG recorder and analyze the scanned ECG data.

Initially, a user/technician 132 provides a medical sensor 116 to the patient 128 to record patient medical data. The user 132 may be a doctor, a clinician, medical personnel, and/or a technician who are in a doctor's office, a clinic, a hospital, or other location remote from the patient 128. The sensor 116 senses a parameter of the patient's body and stores data corresponding to the sensed parameter as patient medical data. The sensor 116 records the patient medical data and stores the patient medical data in a local storage mechanism (not shown) on the sensor 116. This sensor storage mechanism may be local memory or may be a fixed or removable storage medium such as a PCMCIA flashcard. The sensor 116 may be a Holter monitor or recorder that records electrocardiogram (ECG) data of the patient 128 over a period of time. For example, the user/technician 132 provides to the patient 128 the sensor 116 (e.g., the Holter monitor) which records ECG data or Holter data over a period of 24 hours. The Holter monitor is equipped with internal memory for storing the Holter data (not shown). After completing the recording of the patient medical data, the patient 128 returns the sensor 116 to the user 132.

The sensor 116 is also equipped with a communication interface configured to download or transmit the stored patient medical data from the sensor 116 to a remote computer 112, which is remote with respect to the central server 102. The user 132 downloads the sensed patient medical data to the central server 102 via an interface; for example, the sensor 116 may have a Universal Serial Bus (USB) interface 118 that is commonly found on a personal computer. In such an arrangement, the remote computer 112 includes a USB port 119 such that the sensor 116 transfers the patient medical data via its USB interface 118 through the USB port 119 of the remote computer 112 to the central server 102 via a second interface 108. As a result, the patient medical data is transmitted from the sensor 116 to the central server 102. In general, the interface 118 may be any type for transferring data from the sensor 116 to the remote computer 102, such as a serial interface, a parallel interface, a local area network interface, an infrared link, an optical interface, or other hardwired or wireless interface.

In another embodiment, the sensor 116 may also include a removable storage medium or mechanism for storage of the patient medical data. One such removable storage medium is a PCMCIA flash card. The sensor 116 and the remote computer 112 would each be configured for the PCMCIA card. Initially, the card would be positioned within the sensor 116 to store patient data being recorded by the sensor 116. After recording and storage are completed, the PCMCIA flashcard with the stored patient medical data from the sensor 116 is removed from the sensor 116 and inserted into the PCMCIA slot of the remote computer 112. The patient medical data is removed, copied, or transferred by the remote computer 112 to its memory for segmentation and compression. In an alternative embodiment, the PCMCIA card may itself be equipped with the USB interface, in which case the patient medical data is transferred from the PCMCIA card via the USB interface to the remote computer 112. Other memory storage devices are also possible. For example, the sensor 116 and the remote computer 112 may be configured to store and retrieve patient medical data using a floppy disk, a CD-ROM, a memory stick, memory card, or other removable storage medium.

Figure 10A:
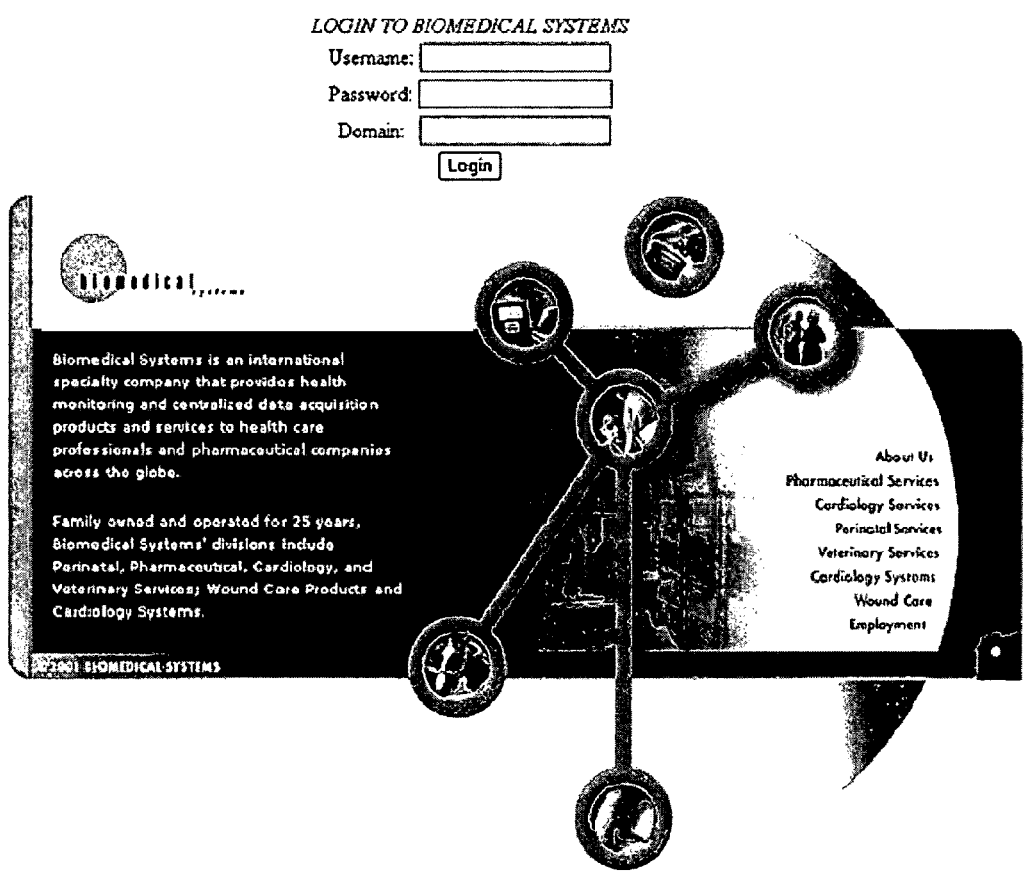
FIGS. 10A to 10E are exemplary screen displays of the transmission of data from a sensor to the central server.
Figure 10B:
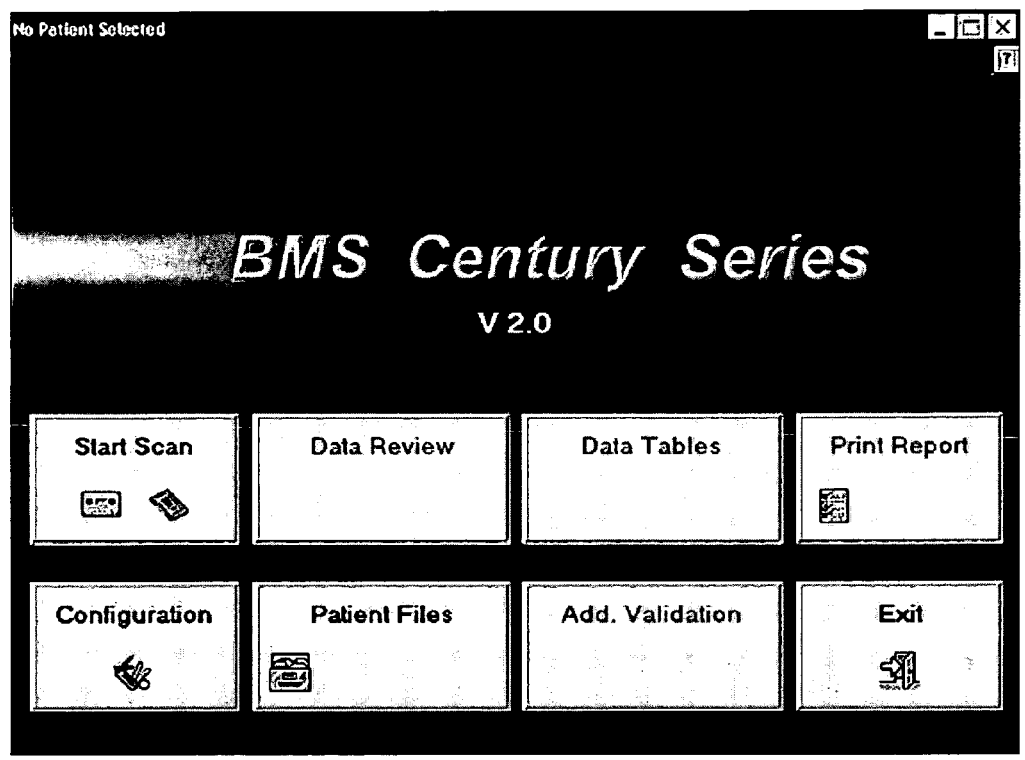
Figure 10C:
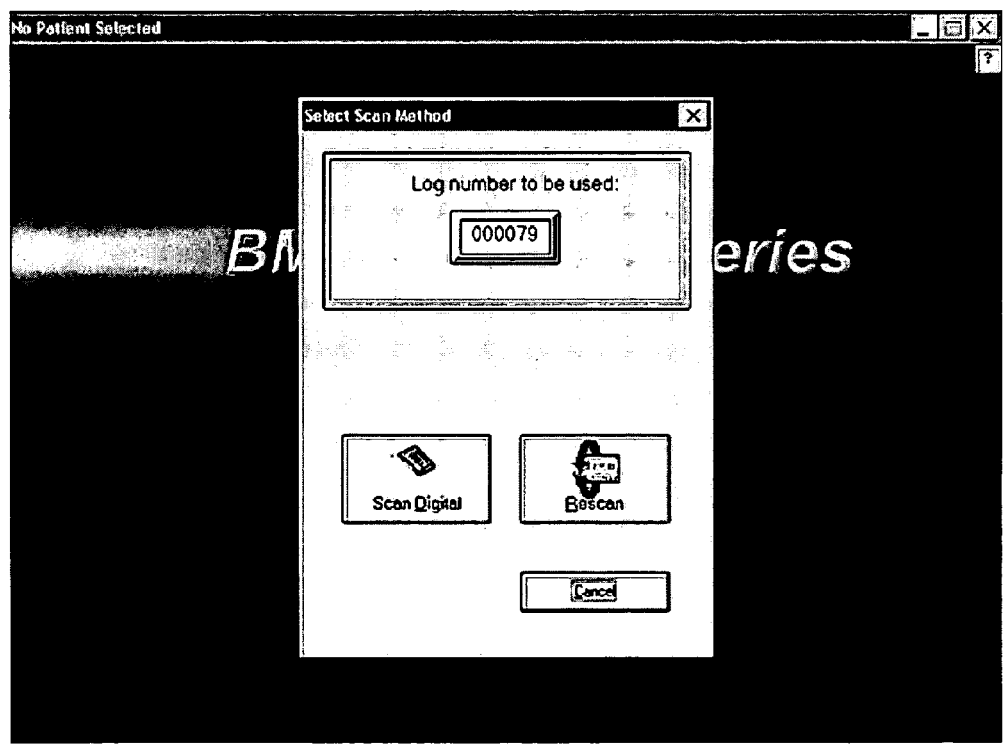
Figure 10D:
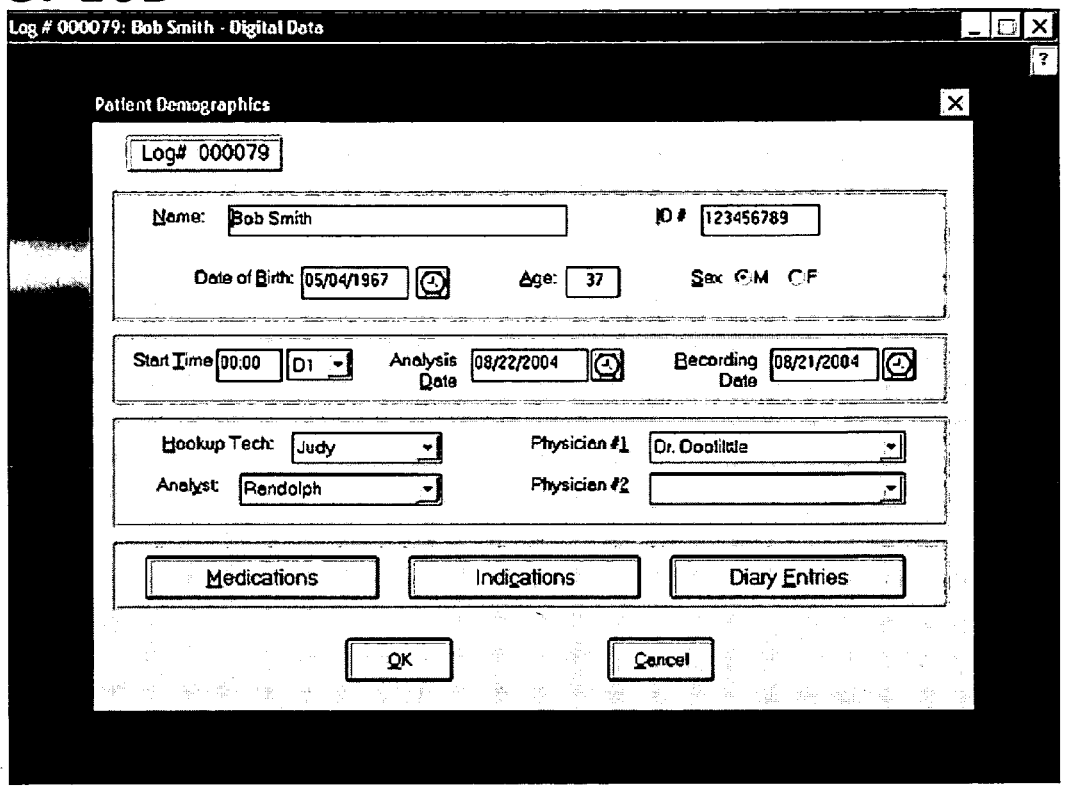
Figure 10E:
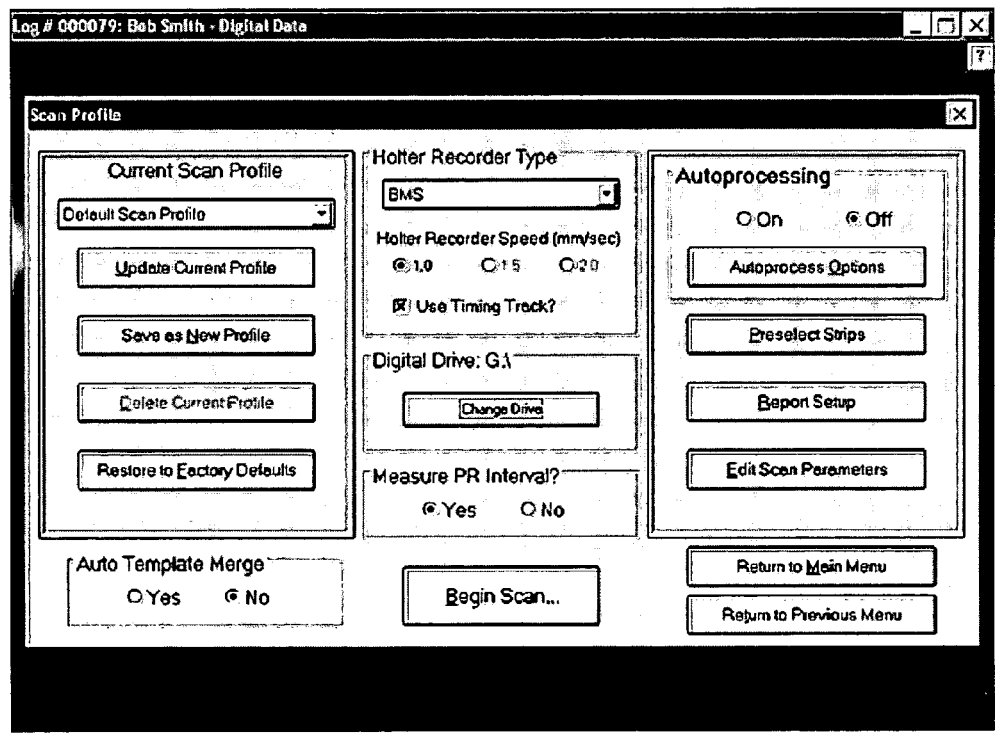

In one embodiment, after connecting the sensor 116 to the remote computer 112 via the USB interface 118, the patient medical data is transmitted to the central server 102. FIGS. 10A to 10E illustrate exemplary screen displays of a user interface illustrating the transmission of data from a sensor to the central server 102. FIG. 10A shows a screenshot of a log-in screen. For example, the user 132 at the remote computer 112 uses logs on to the MyHolter.com via a browser. In another embodiment, the user 132 operates software (e.g., Citrix client application) to logon to the MyHolter.com, by first logging on to the central server (e.g., Citrix® server). By so doing, the central server 102 authenticates the user 132 and assists in assuring that patient medical data transmitted from this remote computer 112 is not commingled with other data in the storage 106 on the central server 102. After the user 132 logs on MyHolter.com and the central server 102, FIG. 10B shows a screenshot providing the user 132 with options for transferring the patient medical data. For example, the user 132 has options such as "Start Scan", "Configuration", "Patient Files" and "Exit". FIG. 10C shows the user 132 has various options in transferring the sensed patient medical data (e.g., ECG data) from the sensor 116 to the central server. For example, when transferring the patient medical data from the sensor 116, a log number is assigned to the transfer and the user 132 has options to "Scan Digital" (e.g., the sensed patent medical data is already in the digital format), and/or "Rescan". FIG. 10D illustrates that the user 132 is presented to enter information about the patient 128. For example, the name of the patient, patient identification number, the patient's date of birth, and/or other demographic information (e.g., "Medication", "Indications", and "Diary Entries" buttons) of the patient 128. The user 132 is further provided with options in FIG. 10E before transferring the sensed patient medical data from the sensor 116 to the central server 102. For example, the user 132 may provide sensor 116 types (e.g., "Holter Record Type"), "Digital Drive", and/or other settings before commencing the transfer.

It is contemplated that FIGS. 10A to 10E illustrate exemplary screen displays of the transmission of data from the sensor 116 to the central server 102 on a display 114 of the remote computer 112. Other display layouts and/or configurations of the options/functions discussed above may be employed. Likewise, other display layouts and/or configurations of screen displays (e.g., FIGS. 11A to 11C, 12A to 12C, and 13A and 13B) may be employed.

In another embodiment, after receiving the patient medical data from the sensor 116, the user 132 stores the received patient medical data on the local storage medium (not shown) of the computer 112. In yet another embodiment, the user 132 may segment the patient medical data and/or compress the segmented patient medical data for improved transmission to the central server 102. For example, patient medical data are usually large data files of more than 10 megabytes of data. The remote computer 112 may be used to optionally compress the patient medical data into a plurality of smaller files such as one-megabyte files. In this case, the plurality of one-megabyte files composing a single patient medical data are identified or named in such a manner as to enable their efficient and effective decompression back into the original patient medical data. Additionally, this optional transmission of the smaller segmented and/or compressed data files improves patient medical data transmission since a transmission error occurring during the transmission will only require the retransmission of a single one-megabyte files, rather than the entire patient medical data file. After optional segmenting and/or compressing, the user 132 transmits the patient medical data on the remote computer 112 through the second interface 108 to the storage 106 on the central server 102.

The communication network 108 connecting the remote computer 112 and the central server 102 may be any communication network capable of transmission of data, such as a public switched network, a public data network, a packet switched data network, an Internet, or a wireless network. The communication network may be the Internet capable of supporting web pages and web page communications. The remote computer 112 may be equipped with an Internet communication interface or service from an Internet Service Provider (ISP) who enables communication of data between the remote computer 112 and any other interconnected computer including the central server 102.

In another embodiment, the second interface 108 is part of software (e.g., Citrix® ICA client) installed in the remote computer 112 that maps the sensor 116 to a particular data storage area of the storage 106 on the central server 102 (e.g., Citrix® server). For example, the central server 102 recognizes the sensor 116 as another data storage or memory device via the USB port 119 and the second interface 108 when the sensor 116 is connected to the computer 112 via the USB port 119. As a result, the second interface 108 permits a direct transmission of the patient medical data from the sensor 116 via the USB port 119 to the central server 102. The second interface 108 next assigns a particular storage area of the storage 106 on the central server 102 for storing the patient medical data received from the sensor 116. With such recognition, the second interface 108 assists in ensuring that the patient medical data of a patient is not commingled with other patient medical data of another patient on the storage 106 on the central server 102.

Figure 11A:
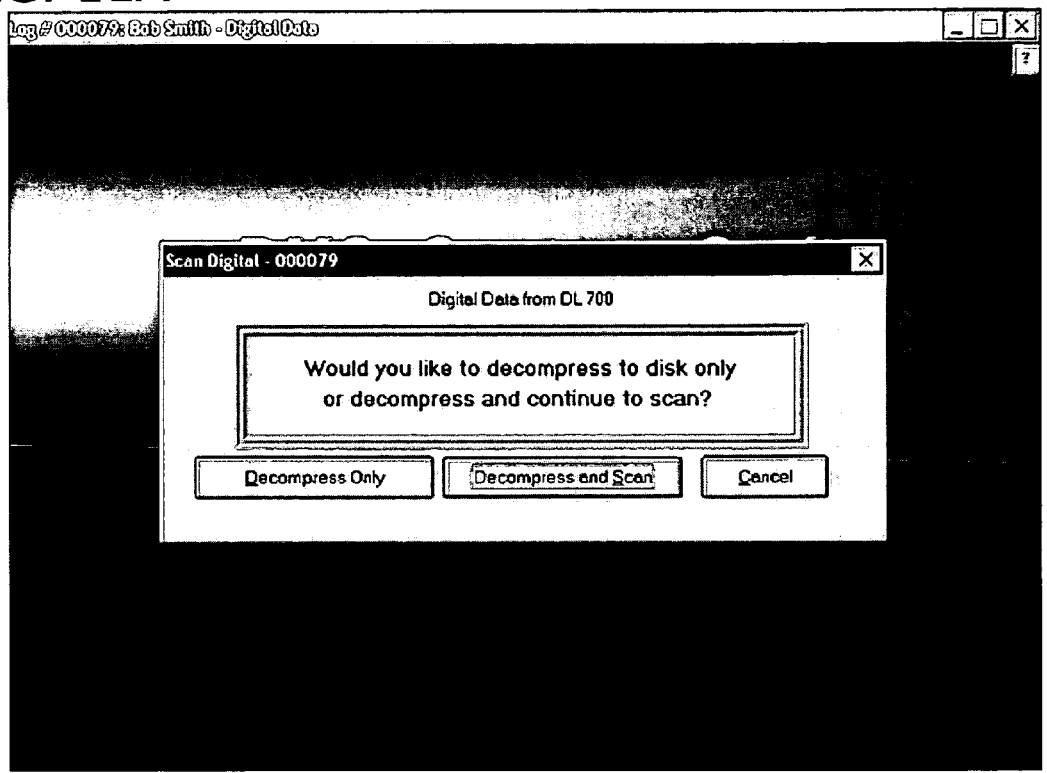
FIGS. 11A to 11C are exemplary screen displays of the second interface according to one embodiment of the invention.
Figure 11B:
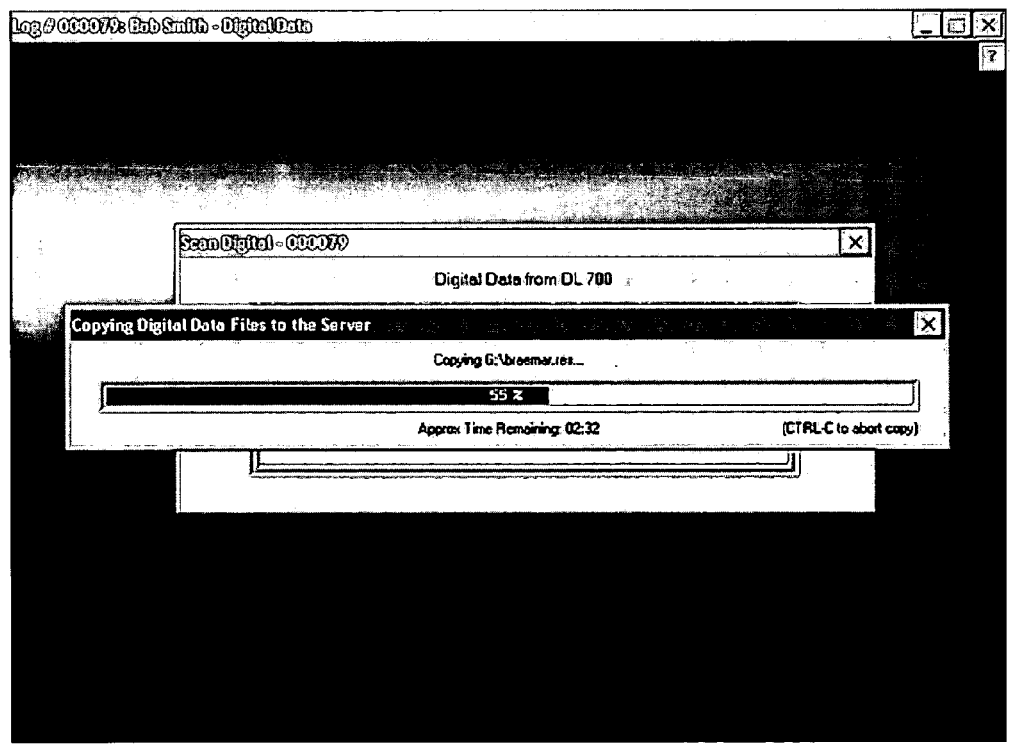
Figure 11C:
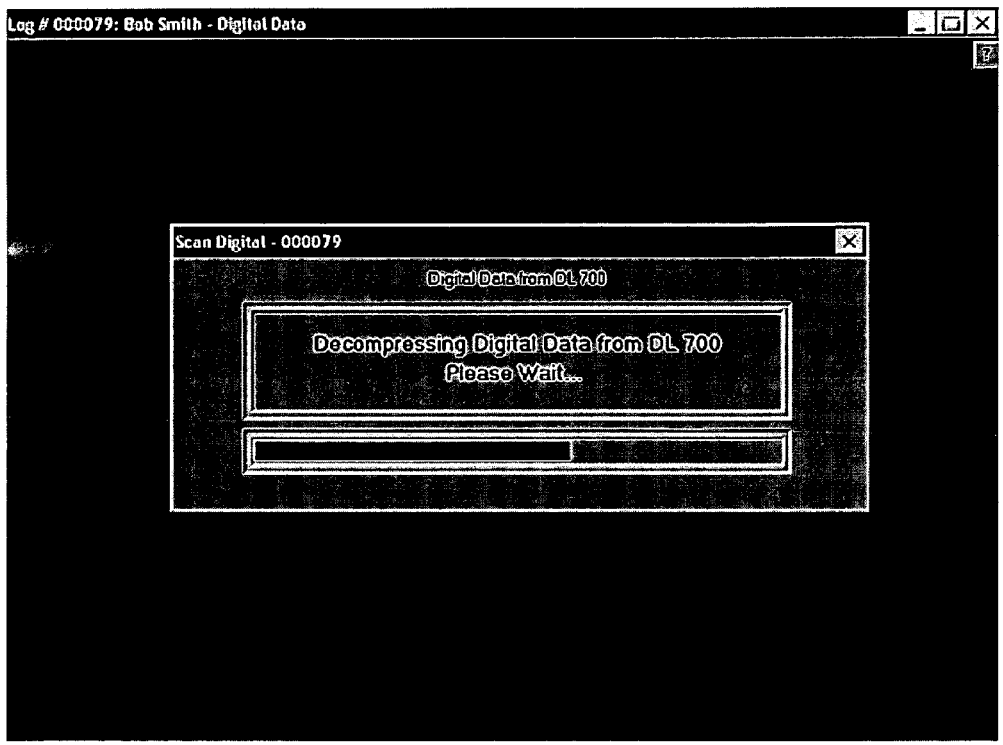

FIGS. 11A to 11C illustrate exemplary screen displays of the second interface 108. FIG. 11A illustrates that the user 132 has an option of decompress the sensed patient medical data (e.g., ECG data) only or decompress and scan the sensed patient medical data when transferring to the central server 102. FIG. 11B shows an exemplary display of progress indicator showing transferring/copying of the sensed patient medical data from the sensor 116 to the central server 102. FIG. 11C shows an exemplary display of decompressing progress indicator of the patient medical data in the computer 112.

In another embodiment, the second interface 108 also includes a web site comprising one or more web pages hosted by the central server 102 which is configured to receive data from and transmit data to the remote computer 112. As such, the remote computer 112 includes an Internet browser or a Citrix® client application for sending the patient medical data from the remote computer 112 to the central server 102. In particular, different layouts and/or configures of FIGS. 11A to 11C may be employed when a web site is used.

The processor 104 of the central server 102 hosts a web site including web pages such that the remote computer 112 located remotely from the central server 102 can access the web pages. When accessing the web pages of the web site (e.g., as myHolter.com) hosted by the central server 102, the user 132 at the remote computer 112 transmits the patient medical data and associated patient information from its memory to the central server 102 through the web pages.

These web pages acting as the second interface 108 permit the processor 104 to receive the segmented and compressed patient medical data and associated patient information received from remote computer 112. The processor 104 decompresses the patient medical data and recompiles the segmented patient medical data and stores the patient medical data and patient information on the storage 106 on the central server 102.

In another embodiment, a remote server (not shown) connected to the communication network between the remote computer 112 and the central server 102 may be employed. The remote server hosts the web page that is accessible by the remote computer 112 configured with a web browser. The remote computer 112 transmits the patient medical data and patient information to the web page of the remote server. The remote server transfers the received patient medical data and patient information to the central server 102 over the communication network to the second interface 108. This optional configuration allows more flexibility. For example, the remote server may be hosted by an Internet Service Provider (ISP) at a central communication hub in the communication network and the central server 102 may be remotely located at a medical institution or medical service provider's location.

It is contemplated that the central server 102 may receive patient medical data from a plurality of sensor 116 and/or remote computers 112 over the communication (to be discussed in detail in FIG. 9). While FIG. 1 only shows a single sensor 116 and a single remote computer 112, in operation a plurality of sensors would provide patient medical data to each remote computer 112. Additionally, a plurality of remote computers 112 may be located at a plurality of widely dispersed medical institutions, all of which are independently connected to the communication network. As such, the plurality of remote computers 112 and the central server 102 communicate over the communication network via the second interface 108 using a secure access that is a minimum of 128-bit secure socket layer connection. In other embodiments, other secure access arrangements may also be incorporated consistent with the invention.

The user 132 uses a third interface 110 to access the analysis software 124 on the central server 102 to analyze the stored patient medical data and/or patient information stored on the central server 102. For example, the third interface 110 may be a series of web pages of a web site (e.g., myHolter.com) hosted by the central server 102 that present a list of options, such as those shown in a user options menu 304 in FIG. 3. In another embodiment, the third interface 110 may be part of software (e.g., Citrix® client) installed in the remote computer 112 that has options in analyzing the stored patient medical data on the central server 102. The processor 104 is configured to use analysis software 124 on the central server 102 to analyze the stored patient medical data. The analysis software 124 provides tools/functions to analyze the stored patient medical data, such as the QT interval, PR interval, or the like of a patient's ECG data.

Figure 12A:
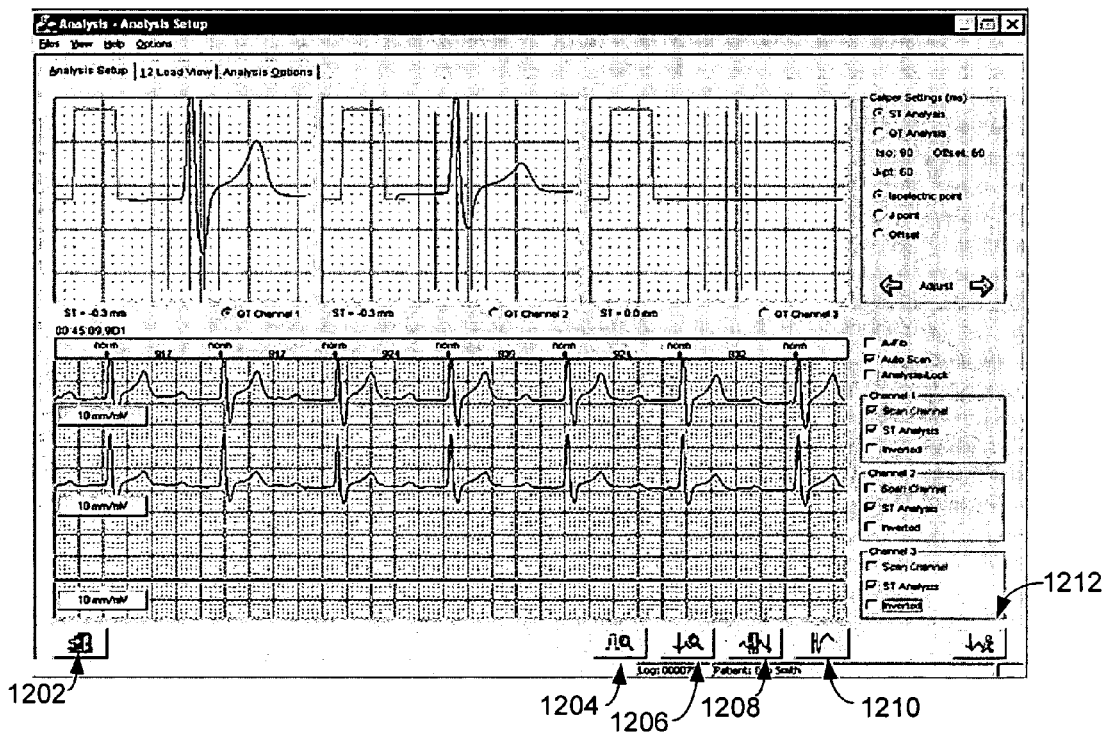
FIGS. 12A to 12C are exemplary screen displays of the third interface according to one embodiment of the invention.
Figure 12B:
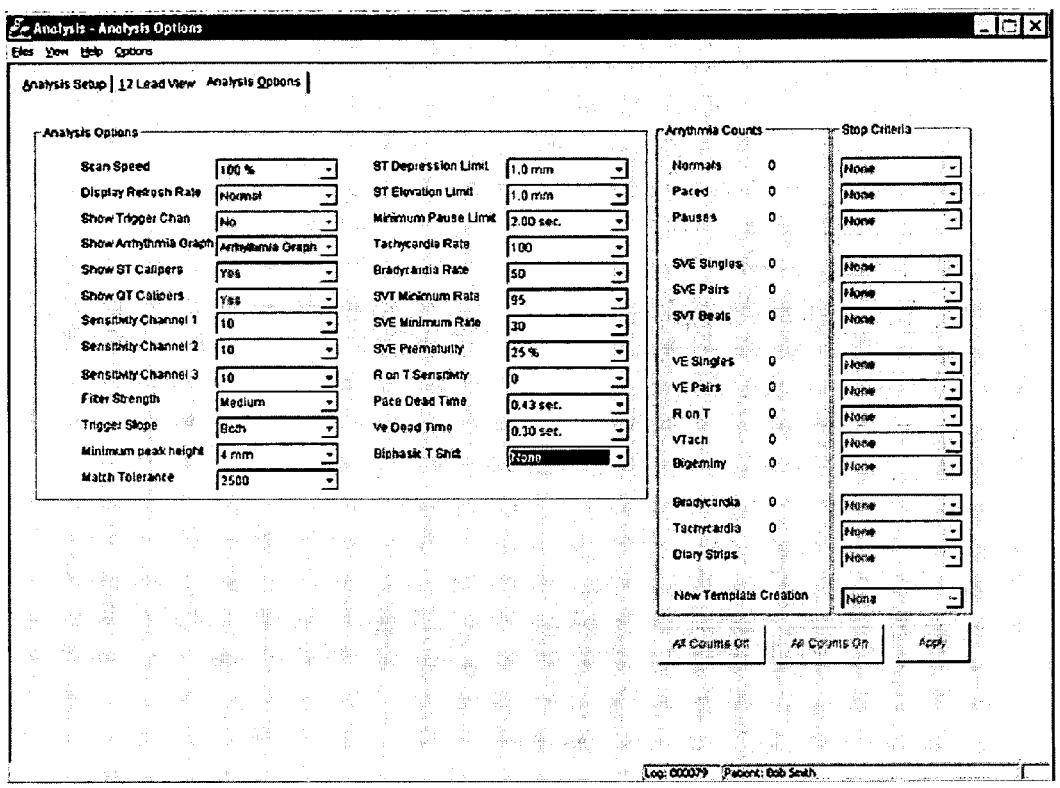
Figure 12C:
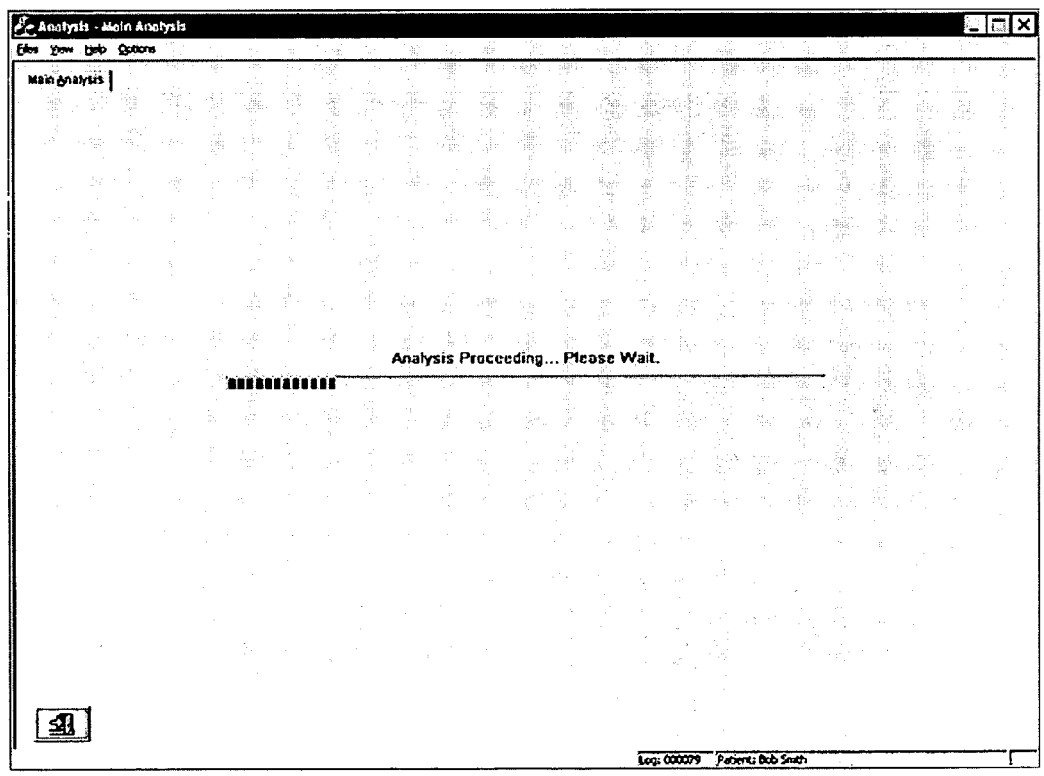

FIGS. 12A to 12C illustrate exemplary screen displays of the third interface 110. FIG. 12A shows an example of various analysis setup parameters (define calibration beat 1204, define normal beat 1206, create beat template 1208, paced beats only analysis 1210, ST analysis, QT analysis, inverted or uninverted) that the user 132 has in using the analysis software 124. For example, FIG. 12A shows the user 132 has an option of different tabs of the patient medical data (e.g., "Analysis Setup", "12 Lead View", or "Analysis Option".) In addition, the user 132 has a list of settings on the right side of FIG. 12A (e.g., ST Analysis, QT Analysis, inverted or the like). Also, other functionalities shown of FIG. 12A are available to the user 132. For example, button 1202 is an "Exit" function which allows the user 132 to exit the program (e.g., MyHolter.com) and the analysis. Button 1204 is a "Find a Better Calibration Beat" function that allows the user 132 to search the data at the beginning of the scan for a better, more consistent calibration pulse. Button 1206 is a "Find Another Normal Beat" function that searches further in the data for a better, more representative normal beat. Button 1208 is a "Create a New Template from the Current Beat" function that allows the user to specifically template any odd or unique morphology. Button 1210 is a "Paced Beats Only Analysis" function which may be used if the user/technician 132 expects the data is from a pacer-only patient. Button 1212 is a "Start Analysis" function that launches the user into the analysis depicted by the progress bar in FIG. 12C. FIG. 12B shows a screenshot of the "Analysis Options" in which the user 132 can determine different analysis options (e.g., ST Depression Limit, ST Elevation Limit, Minimum Pause Limit, Tachycardia Rate, Bradycardia Rate, Supraventricular Tachycardia (SVT) Minimum Rate, Supraventricular Ectopic (SVE) Minimum Rate, Supraventricular Ectopic (SVE) Prematurity, or the like) before analyzing the patient medical data.

It is to be understood that the analysis of the patient medical data may not occur immediately after the patient medical data is stored on the storage 106 of the central serve 102. The user 132 may store unanalyzed patient medical data on the central server 102 for later analysis. In one embodiment, there may be a storage limit of unanalyzed patient medical data on the storage 106 of the central server 102.

Figure 13A:
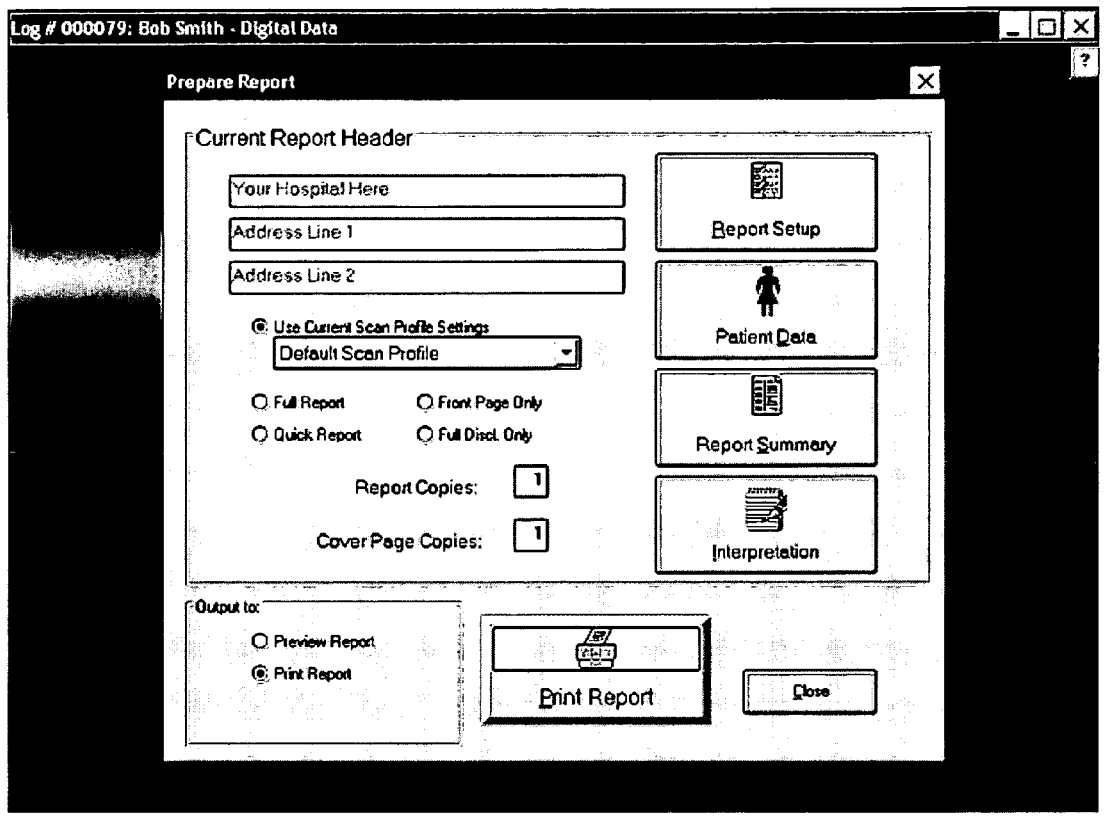
FIGS. 13A to 13B are exemplary screen displays of the fourth interface according to one embodiment of the invention.
Figure 13B:
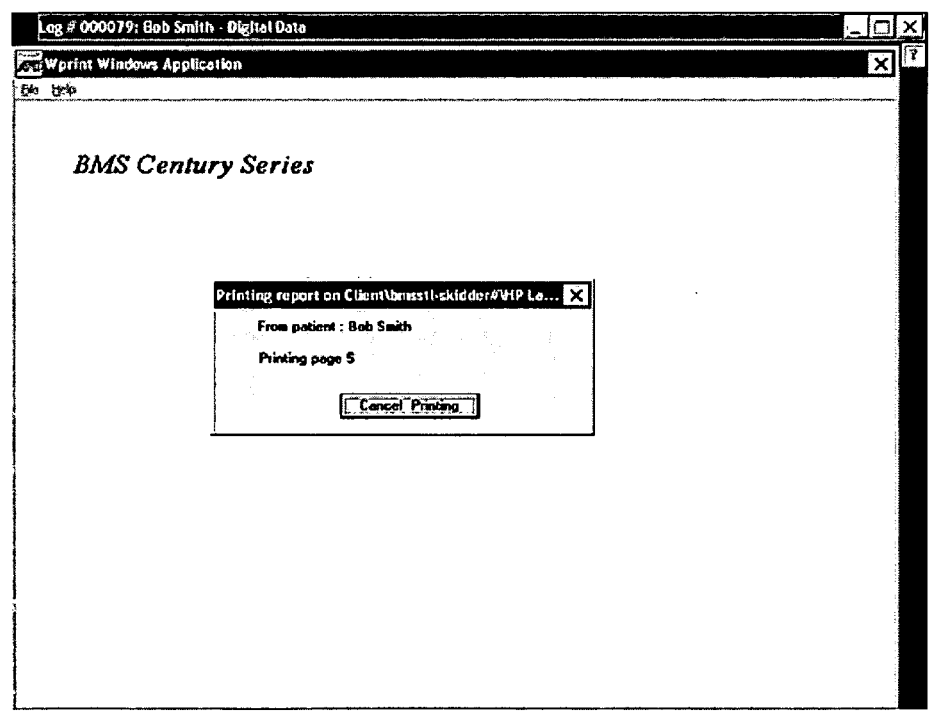

After the analysis of the stored patient medical data by the analysis software 124, the user 132 uses a fourth interface 120 to transfer a medical report, resulting from the analysis of the patient medical data, from the central server 102 to the remote computer 112. FIGS. 13A and 13B illustrate exemplary screen displays of the fourth interface 120. FIG. 13A shows various options to the user 132 in preparing the medical report. For example, the user 132 may choose "Report Setup", "Patient Data", "Report Summary" and "Interpretation" options before printing the report. The user 132 also has the option of previewing the report by selecting the option "Preview Report" on the bottom left corner of FIG. 13A. FIG. 13B shows an example of printing progress indicator as the user 132 transfers the medical report from the central server 102 to the remote computer 112.

The user 132 transmits the medical report from the central server 102 to the remote computer 112 which displays the medical report on the display 114, stores the medical report on a local storage medium (not shown), or prints the report on a local printer (not shown) associated with the remote computer 112.

Figure 2:
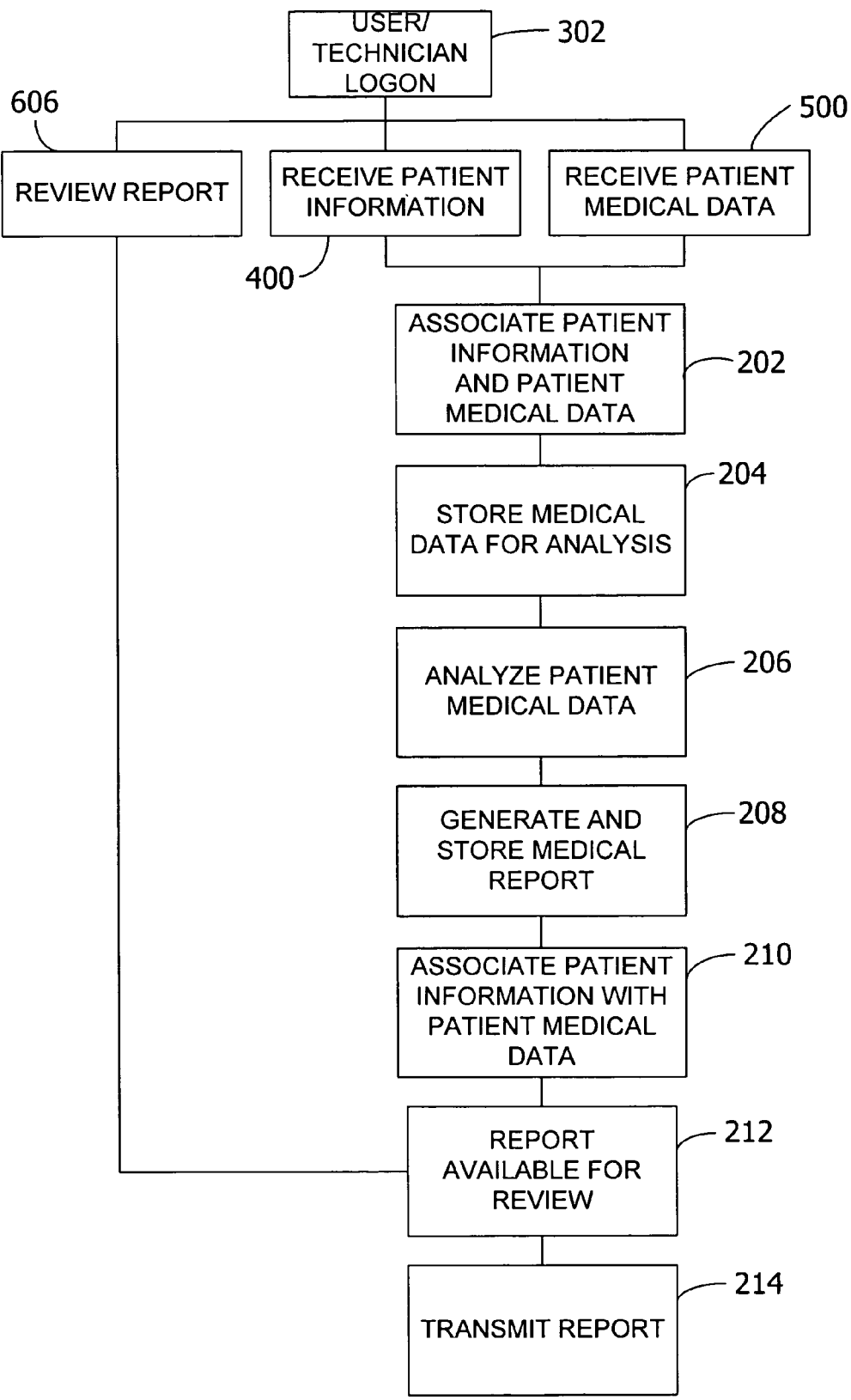
FIG. 2 is a block diagram illustrating a method of acquiring and controlling the access to and analysis of patient medical data over a network by a central server according to one embodiment of the invention.

FIG. 2 illustrates one process for analyzing patient information, patient medical data, and medical reports by the central server 102. The user 132 logs onto the central server 102 at 302. The central server 102 may receive patient information at 400 from the logged on user 132 or receive patient medical data at 500. The central server 102 associates the received patient medical data with patient information at 202. The patient information may be pre-existing patient information or new patient information added via 400. At 204, the user 132 stores each patient medical data in a particular part of the storage 106 of the central server 102. Next, the central server 102 makes the patient medical data available for analysis using the analysis software 124. Once the user 132 selects a particular file or files of patient medical data for analysis, the user 132 at 206 uses the analysis software to analyze the patient medical data on the central server 102. The central server 102 may restrict access to a particular patient medical data file. After analyzing the stored patient medical data at 206, the analysis software 124 generates a medical report at 208.

The central server 102 also stores the medical report on the storage 106 at 208 and associates it with the corresponding patient medical data and the patient information at 210. Once the medical report is associated with the patient information, the medical report is made available to one or more users 132 at computers 112 based on pre-established authorization and notification assignments (e.g., user logins) at 212. The user 132 may request one of the stored medical reports at 606 using the "review results" process discussed later in FIG. 6. If the user selects to review the medical report at 606, the central server 102 transmits the medical report at 214 to the computer 112 associated with the requesting user 132 over the first network 110.

In operation, the medical data of the patient 128 is recorded at the site of the patient 128 with the sensor 116. A local medical care provider such as a physician at a local medical office provides the patient 128 with the sensor 116. The patient 128 uses the sensor 116 such as an electrocardiogram (ECG) data recorder or the Holter monitor/recorder to record ECG data over a defined period of time (e.g., 24 hours). The patient 128 wears the monitor at home or work during normal daily activity. After the defined period of time has elapsed and the recording is complete, the patient 128 returns to the medical office or facility with the sensor 116 or directly accesses a remote computer 112 and the necessary acquisition software as discussed above and below. The sensor 116 has the patient medical data stored internally in memory or on a removable storage format. The user 132 of the remote computer 112 is a medical technician, medical assistant, doctor, or may be the patient 128. The remote computer 112 is configured with software designed to retrieve and manage the patient medical data. As noted earlier, a software configuration consistent with this invention is the patient medical data acquisition, and program for transmitting patient medical data from the sensor 116 to the central server 102. Alternatively, a software process may also comprise storing the patient medical data on the remote computer 112, compressing the medical data, and transferring the patient medical data from the remote computer 112 to the central server 102. The connection between the sensor 116 and the remote computer 112 is configured such that the central server 102 may operate the sensor 116 as a removable drive for transferring the patient medical data. Alternatively, the remote computer 112 is configured such that the storage format and patient medical data as presented is seen as a removable drive on the remote computer 112.

As noted above, the remote computer 112 is configured with the web browser or other data communication interface (e.g., Citrix® client application), such as a second interface 108. The user 132 of the remote computer 112 logs onto the central server 102 through a secure access connection such as a secure socket layer connection with a 128-bit minimum encryption. This provides secure access to the central server 102 and the transmitted patient medical data and the patient information. In an embodiment where the Citrix® client application is used, the central server 102 (e.g., a Citrix® server) also authenticates the Citrix® client application in the remote computer 112, as seen in FIG. 10B. The central server 102 hosts a web page and receives the patient medical data via the web page from the remote computer 112 configured with the web browser. The central server 102 stores the received patient medical data and patient information on the storage 106. As described above, the user 132 via the third interface 110 uses the analysis software 124 on the central server to analyze the stored patient medical data. The analysis software 124 generates the medical report associated with the patient medical data and stores the medical report on the central server 102. The central server 102 associates the medical report with the patient information and patient medical data and provides selective access to the medical report from one or more computers 112 or users 132 of computers 112. The central server 102 transmits or provides access to the medical report by the remote computer 112 via the fourth interface 120.

Figure 3:
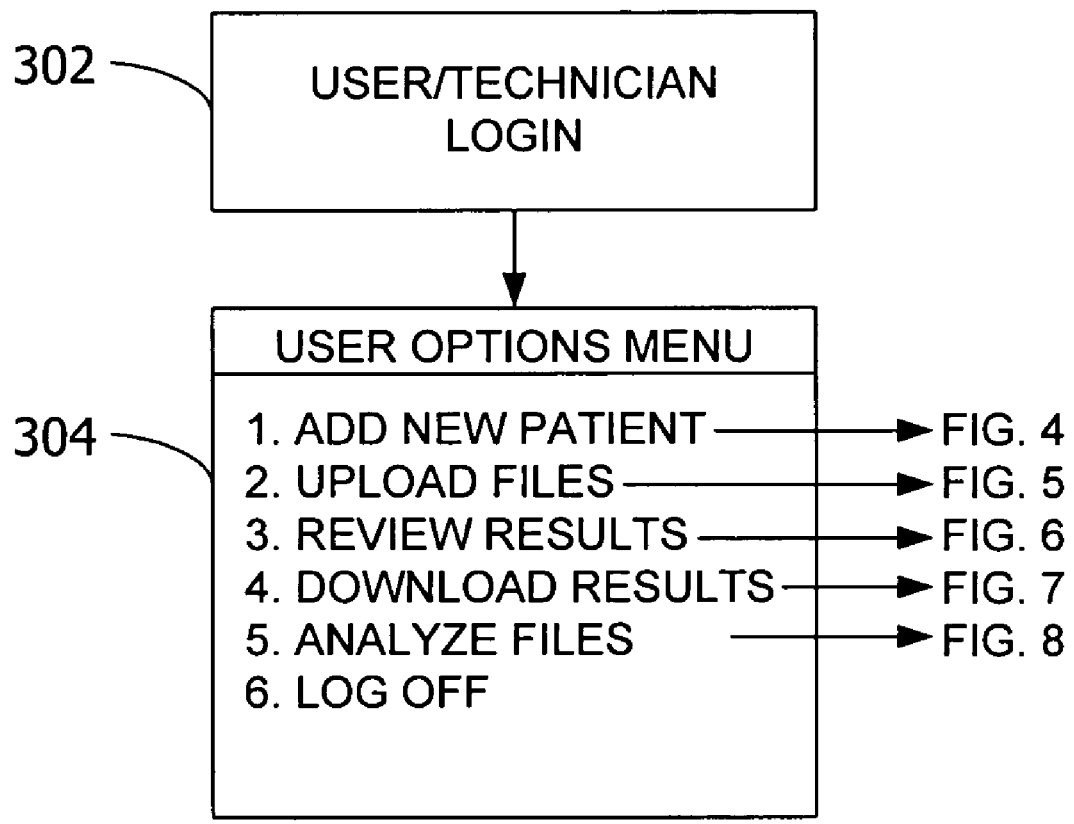
FIG. 3 is a block diagram illustrating the user options menu for initiating the acquisition and analysis of patient medical data over a network according to one embodiment of the invention.

FIG. 3 illustrates the user login screen 302 that is presented to the user 132 of the remote computer 112 when the user 132 logs into the central server 102. Once the user 132 logs in, the user 132 is presented with a user options menu 304. The list of available options for user 132 are defined by the central server 102 based on a pre-establish list of authorized functions or activities based on the user identification number. For example, a medical assistant 132 in a medical office may operate the remote computer 112 to upload patient medical data. The medical assistant user 132 may not be authorized to view the associated medical reports once completed. However, the attending physician may be notified of the availability of the medical report, and may access the system to view the medical report. Generally, the user 132 may select one of the options from the "users option menu": (1) add new patient, (2) upload patient medical data, (3) review a medical report, (4) download a medical report, (5) analyze files, or (6) log off. FIGS. 4 to 8 illustrate processes associated with each of these user options respectively.

Figure 4:
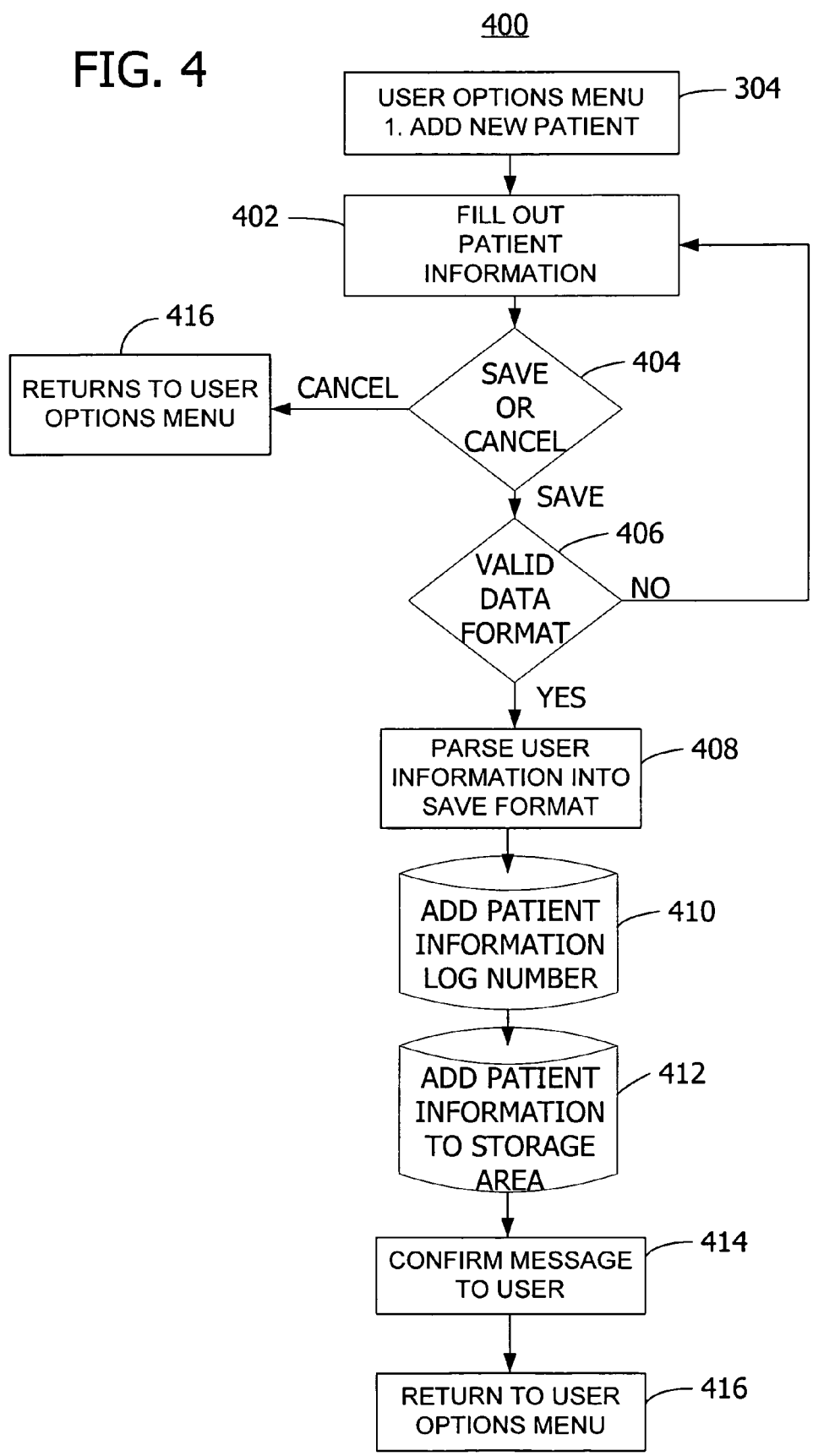
FIG. 4 is a block diagram illustrating the process of adding a new patient according to one embodiment of the invention.

FIG. 4 illustrates the "add new patient" process 400 as selected by the user 132 on the "user options menu" 304, the user is prompted to supply the patient information at 402. The central server 102 presents the user 132 with a series of user information screens. The user 132 interacts with the web page hosted by the central server 102 or optional remote server 130 and enters the patient information. The user 132 is then requested to save or cancel the entered data at 404. If the user 132 selects to cancel, the user 132 is returned at 406 to the user options menu 304. If the user 132 selects to save, the central server 102 verifies the validity of the data format at 406. If the data is not in a valid format, the user 132 is returned to the patient entry at 416. If the data is valid, the central server 102 parses the patient information into a save format at 408 and adds the patient information to a database at 410. The method further adds a log number to the patient information at 412 when the information is stored and sends a confirmation message at 414 to the user 132. Once this is complete, the central server 102 returns the user 132 at 416 to the user options menu 304. The user 132 need only complete the "add new patient" process of 400 for a patient 128 that is new to the central server 102. If the patient information already exists in the central server 102 for a patient 128, this process is not required. At this point, the user 132 may upload the patient medical data, such as the Holter data to the central server 102 from the computer 112.

Figure 5:
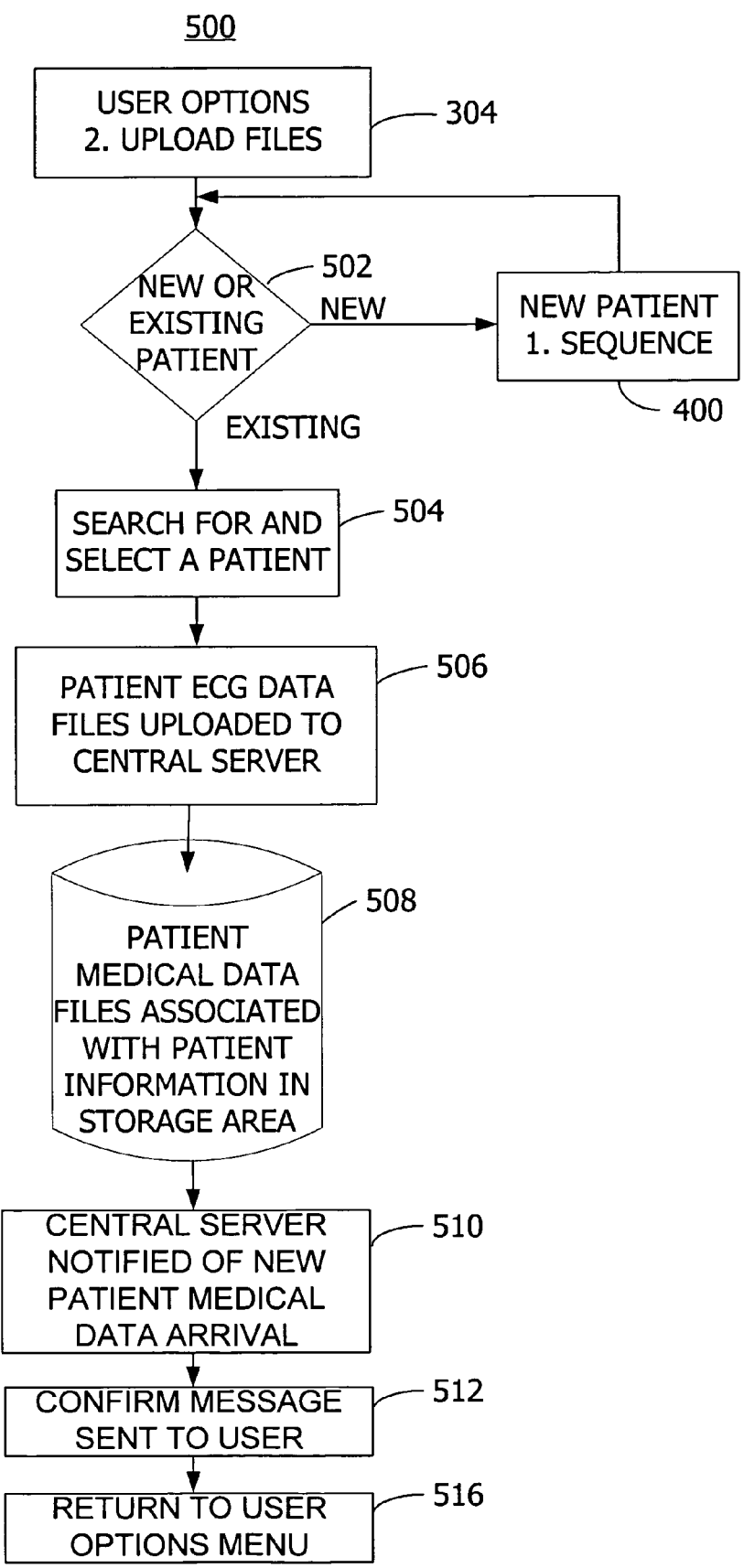
FIG. 5 is a block diagram illustrating the patient medical data upload process according to one embodiment of the invention.

Referring now to FIG. 5, when the user 132 of the remote computer 112 selects the "upload files" process 500 from the user options menu 304, the user 132 is prompted to select either a new or existing patient 128 at 502. If a new patient 128, the user 132 is directed to the new patient sequence 400 as discussed above. If an existing patient 128, the user 132 is offered a list of patients at 504. Of course, the list of patients offered to a particular user 132 by the central server 102 is limited based on the user authorization identified when the user 132 logged into central server 201. When the user 132 selects a particular patient 128, the sensor 116 or the remote computer 112 uploads the patient medical data to the central server 102 at 506 and the central server 102 receives the uploaded files. The transmission of the patient medical data from sensor 116 or the remote computer 112 to the central server 102 may occur immediately or may be delayed to a later time. For instance, the transmission of the patient medical data may be delayed to be sent after business hours, when the need or usage of the remote computer 112 or first network 110 is less. When the remote computer 112 has compressed the patient medical data into segmented compressed files prior to transmission to the central server 102, the central server 102 decompresses the received compressed patient medical data and recompiles the patient medical data to the state it was before being compressed by the remote computer 112. The central server 102 associates the patient medical data with the patient information and stores the patient medical data in storage 106, as discussed above and shown at 508. Once the patient medical data is stored and ready for access, the central server 102 is notified of new patient medical data at 510 and a confirmation message is sent to the user 132 at the remote computer 112 at 512. The user 132 operating the remote computer 112 is returned to the user options menu 304 at 416.

Figure 6:
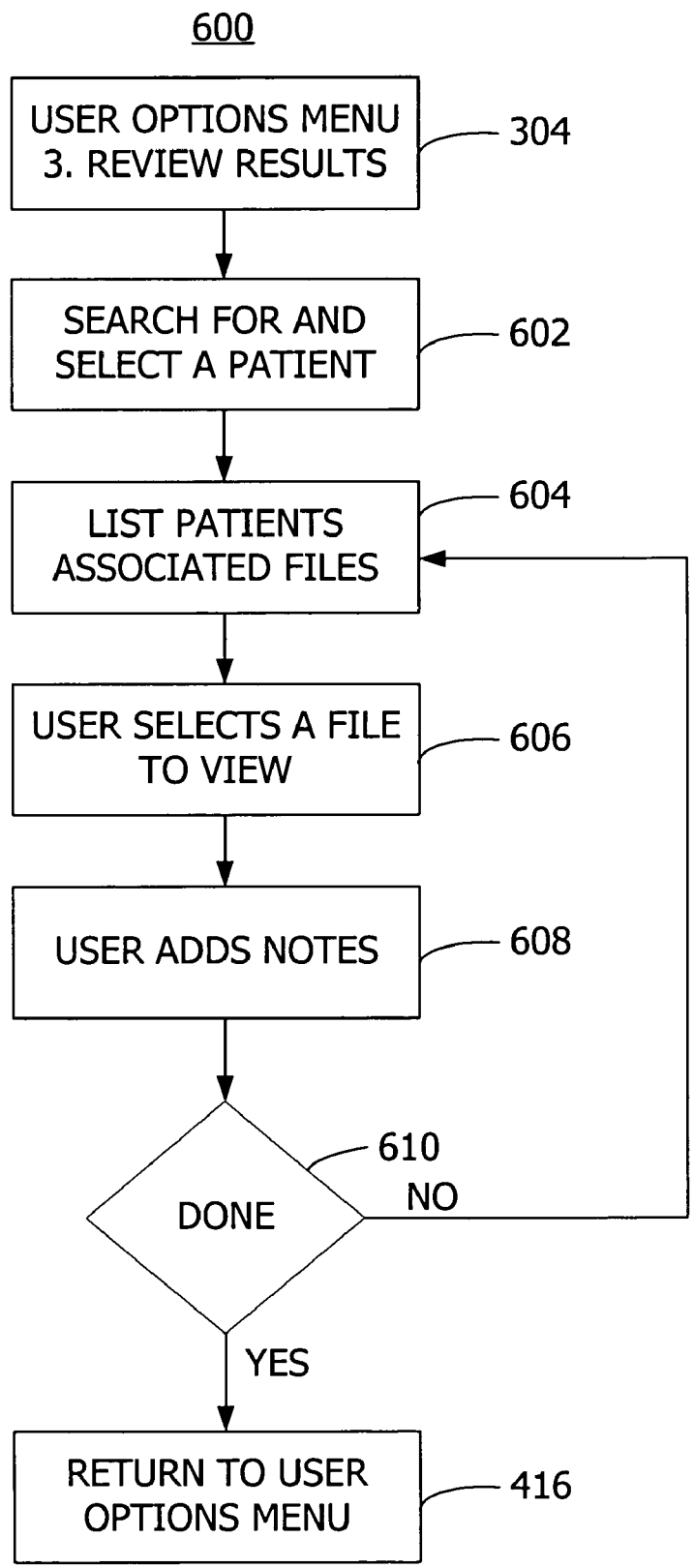
FIG. 6 is a block diagram illustrating the method of transmitting a medical report associated with patient medical data and patient information to the remote computer according to one embodiment of the invention.

Referring now to FIG. 6, when the user 132 selects the "review results" process 600 from the user options menu 304, the user 132 of the remote computer 112 searches for a particular medical report associated with a particular patient 128 and selects the patient 128 or the medical report at 602. The central server 102 provides the remote computer 112 with a list of available completed medical reports and associated files at 604. The user 132 selects one of the available medical reports to view at 606. Once the user 132 has viewed the medical report, the user 132 may add notes to the medical report or to an associated report or file at 608. When this is complete at 610, the user 132 may choose to view another medical report or return to the user options menu 304 at 416.

Figure 7:
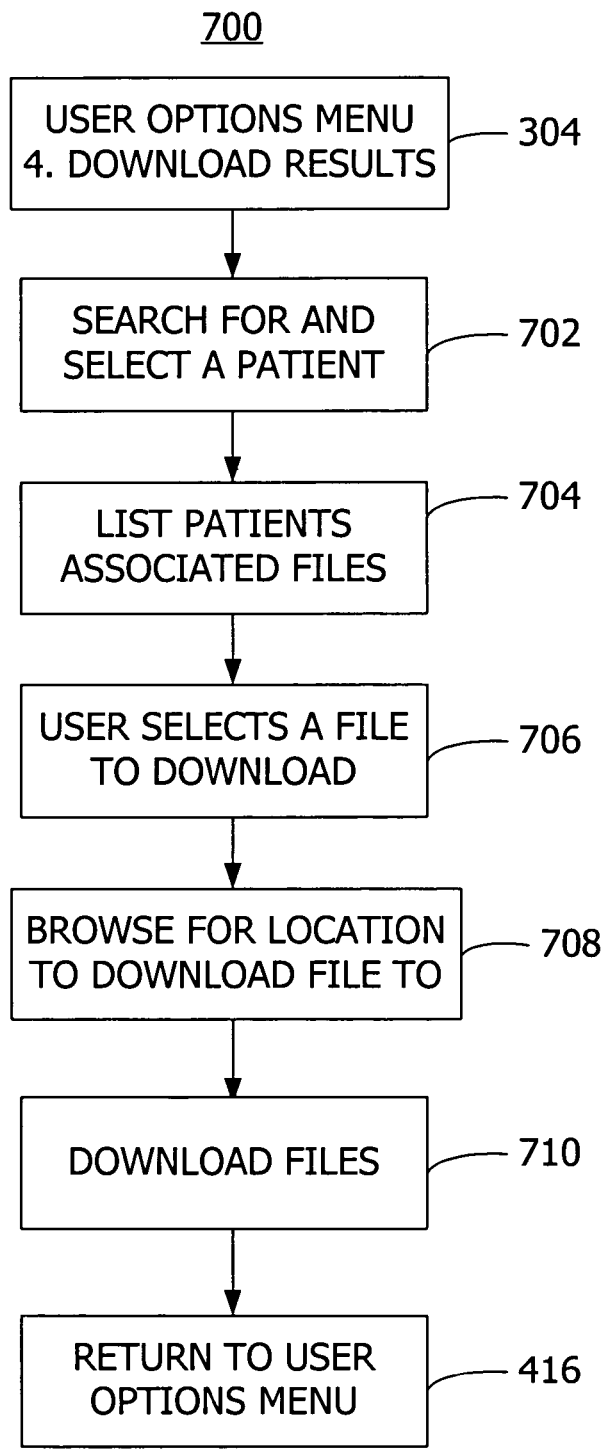
FIG. 7 is a block diagram illustrating the method of downloading a medical report associated with patient medical data and patient information to the remote computer according to one embodiment of the invention.

Referring now to FIG. 7, when the user 132 selects the "download results" process 700 from the user options menu 304, the user 132 searches for a particular patient 128 at 702. The central server 102 lists the patients 128 available to the user 132 and the associated files at 704. From the list presented by the central server 102, the user 132 selects a file to download at 706. The user 132 selects a memory or storage location associated with the remote computer 112 to download the file to at 708 and initiates the download process. The central server 102 downloads the selected file via the first communication interface 108 over the first network 110 to the remote computer 112 at 710. Once the download has been complete, the central server 102 returns the user 132 at 416 to the user options menu 304.

Referring now to FIG. 8, when the user 132 selects the "analyze files", the user 132 instructs analysis software 124 to analyze the patient medical data. It is understood that the user 132 may only analyze or may only have access to the patient medical data or data files that are associated with the login parameter/permission of the user 132 at 302 in FIG. 3. The user 132 scans the stored patient medical data using the analysis software 124 on the central server 102 at 806. At 808, the user 132 is presented with an option of performing the analysis immediately or storing the patient medical data without analysis. If the user 132 chooses to analyze the patient medical data at a later time, the unanalyzed data is stored in the storage 106 at 810. The storage for unanalyzed patient medical data may be limited. On the other hand, if the user 132 decides to perform the analysis, the analysis software 124 analyzes the stored patient medical data at 814. The patient medical data may be Holter data from a Holter monitor and the analysis software 124 may be a Holter program to perform a Holter analysis of the Holter data. At 816, the Holter analysis of the medical report includes one or more data files including a Portable Document File (PDF) file containing the Holter analysis report. When the Holter analysis process and resulting medical report are complete, the central server 102 stores the medical report on storage 106. The central server 102 makes the medical report (e.g., Holter report) available to the user 132 for viewing or printing. The medical report may be in a PDF file format, which is absorbed into the storage 106 as an object. Other associated files may be included in the database or stored in other storage 106 controlled by the processor 104.

When the central server 102 receives the medical report, the central server 102 notifies the associated or designated remote computer 112 that the medical report is complete and available for access and review. The remote computer 112 receives the notification and is provided access to the medical report. Controlled access by the central server 102 to the medical report is made in several different ways including viewing the report in a view mode from the remote computer 112 equipped with a web browser. Another method is for the remote computer 112 equipped with PDF-format reader, to view the document. The remote computer 112 displays the PDF-formatted medical report on display 114, stores the medical report locally, or prints the medical report on an associated printer (not shown). In another method, the medical report is transmitted as an electronic file by the central server 102 to the remote computer 112 via the first communication interface 108 over the first network 110.

FIG. 9 is a block diagram illustrating a plurality of users at sites 910 accessing the central server 902 for analyzing patients' medical data for patients according to one form of the invention. A site 910-1 is a location, such as a doctor's office, a clinician's office, a hospital, or a patient's home where a patient's medical data (e.g., Holter data) may be collected by a workstation at the site 910-1. Similarly, a site 910-X is also another location where another patient's medical data is gathered and acquired. It is to be understood that there may be a number of site 910 where the patient medical data is gathered and received. By way of example and not limitation, a Holter data acquisition/playback device (e.g., sensor 116 in FIG. 1), a printer, and a workstation are shown in FIG. 9 in each site 910. It is contemplated that there may be multiple Holter data acquisitions at each site 910. In one embodiment, the patient 128, the sensor 116, the user/technician 132, the remote computer 112 and the display 114 in FIG. 1 are located at site 910.

A playback device (e.g., the sensor 116 in FIG. 1) transfers the patient medical data to the central server 102 or to a workstation 914-1 (e.g., remote computer 112 in FIG. 1). As discussed above, the user 132 logs onto a web site (e.g., myHolter.com) hosted by the central server 902 or logs onto the central server 902 via an application installed in the workstation 914-1 (e.g., Citrix® client). A firewall 912-1 assists in ensuring a secure access/session while the user 132 is logged on. Via an interface 906, the patient medical data is transferred from the playback device (e.g., the sensor 116 in FIG. 1) to the central server 902. It is contemplated that the interface 906 includes the second interface 108, the third interface 110, and the fourth interface 120 in FIG. 1. In addition, as a result of the login by the user 132 at the site 910-1, the central server 902 is configured to assign a site-specific instance of an online Holter program and a unique server storage location for site 01. As such, another user at site X will access a specific instance of an online Holter program and a unique server storage location assigned for the site X. With this implementation, the central server 102 further assists in ensuring a secure access of a uniquely assigned storage area on the central server 102.

The invention is also a method for managing the receipt and analysis of Holter monitor patient medical data received at the remote computer 112 and analyzed the patient medical data on the central server 102 by using the analysis software 124 on the central server 102. At the site of the patient 128, patient medical data is recorded on the sensor 116 and is stored on a local storage medium. The patient medical data is transmitted to the remote computer 112. At the remote computer 112, new patient information is created that corresponds to the patient medical data. The patient medical data is received from the sensor 116 and stored on the remote computer 112. The remote computer 112 segments and/or compresses the patient medical data and transmits the segmented and/or compressed patient medical data and corresponding patient information to the central server 102.

The central server 102 receives the segmented and/or compressed patient medical data and corresponding patient information. The central server 102 decompresses and/or compiles the patient medical data and stores the patient medical data and patient information in storage 106. A processor 104 associated with the central server 102 controls the access to the patient medical data and patient information. The user 132 analyzes the patient medical data using the analysis software 124 on the central server 102. Based on this analysis, the central server 102 generates the medical report and stores the medical report. Processor 104 controls access to the medical report. The central server 102 transmits the medical report to the remote computer 112. The remote computer 112 receives the medical report from the central server 102 and displays the medical report.

When introducing elements of the present invention or preferred embodiments thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above exemplary constructions and methods without departing from the scope of the invention, it is intended that all matter contained in the above description or shown in the accompanying drawings shall be interpreted as illustrative and not in a limiting sense. It is further to be understood that the method steps described herein are not to be construed as necessarily requiring their performance in the particular order discussed or illustrated. It is also to be understood that additional or alternative steps may be employed consistent with the present invention.

What is claimed is:

1. A method for analyzing ECG data of a plurality of patients over a network, said method comprising:
   establishing a first connection between a central server and a first device having access to a first ECG data of a first patient at a first remote site, said first remote site being remote with respect to the central server;
   transferring the first ECG data from the first device to the central server via the established connection;
   storing the first ECG data in a data storage area of the central server;
   providing by the central server a user interface to a first user at a first analysis site, said provided user interface enabling the first user to interact with the stored first ECG data on the data storage area of the central server without downloading the stored first ECG data to the first user at the first analysis site, said first analysis site being remote with respect to the central server and the remote first site;
   receiving first instructions from the first user at the first analysis site via the provided user interface for the central server to execute ECG analysis software, wherein the received first instructions from the first user include first analysis setup parameters and first analysis options for configuring the ECG data analysis software on the central server for analyzing the stored first ECG data on the central server;
   in response to and in conjunction with the received instructions, analyzing the stored first ECG data on the central server based on the received first analysis setup parameters and first analysis options without downloading the stored ECG data from the central server to a computing device separate from the central server, and generating a first report on the central server based on said analyzing the stored first ECG data;
   transmitting the first report related to the analyzed first ECG data from the central server to the first user;
   establishing a connection between the central server and a second device having access to a second ECG data of a second patient at a second remote site, said second ECG data different from the first ECG data, said second remote site being remote with respect to the central server and with respect to the first remote site;
   transferring the second ECG data from the second device to the central server via the established connection;
   storing the second ECG data in the data storage area of the central server;
   providing by the central server the user interface to a second user at a second analysis site, said second user different from the first user, said provided user interface enabling the second user to interact with the stored second ECG data on the data storage area of the central server without downloading the stored second ECG data to the second user at the second analysis site, said second analysis site being remote with respect to the central server, the first analysis site, the remote first site and the remote second site;
   receiving second instructions from the second user at the second analysis site via the provided user interface for the central server to execute ECG analysis software, wherein the received second instructions from the second user include second analysis setup parameters and second analysis options for configuring the ECG data analysis software on the central server for analyzing the stored second ECG data on the central server;
   wherein the second analysis setup parameters received from the second user are different from the first analysis setup parameters received from the first user and the second analysis options received from the second user are different from the first analysis options received from the first user;
   in response to and in conjunction with the received second instructions, analyzing the stored second ECG data on the central server based on the received second analysis setup parameters and second analysis options without downloading the stored ECG data from the central server to a computing device separate from the central server, and generating a second report on the central server based on said analyzing the stored second ECG data, said second report different from the first report; and
   transmitting the second report related to the analyzed second ECG data from the central server to the second user wherein the central server analyzes two different ECG data in two different ways as specified by two different users so that the first ECG data is analyzed according to the first analysis setup parameters and the first analysis options specified by the first user and so that the second ECG data is analyzed according to the second analysis setup parameters and the second analysis options specified by second first user.

2. The method of claim 1 wherein transferring comprises the sensed ECG data is transferred from the sensor via a port on a remote computer over the communication network to the central server so that the ECG data is stored on the central server and is not stored by the remote computer.

3. The method of claim 1 wherein the sensor corresponds to a mapped drive and wherein transferring the sensed ECG data from the computer to the central server comprises transferring the data from the sensor to a storage area of the central server without intermediate storage.

4. The method of claim 1 further comprising registering the user at a web page of the user interface, wherein the central server is configured for hosting the web page and wherein the computer is configured with a web browser for accessing the web page and displaying analysis options to analyze the sensed ECG data through the web page to be sent to the ECG data analysis software on the central server.

5. The method of claim 1 wherein each device is a sensor configured to sense the ECG data from the patient, and said storing includes transferring the ECG data from the sensor to the data storage area without intermediate storage.

6. The method of claim 1 wherein each device is a computer with access to a sensor configured to sense the ECG data of the patient.

7. The method of claim 1 wherein providing comprises providing a web page of the user interface hosted by the central server and for displaying the analysis setup parameters and the analysis options to be used to analyze the ECG data.

8. The method of claim 7 wherein the analysis options include at least one of ST depression limit, ST elevation limit, minimum pause limit, tachycardia rate, bradycardia rate, supraventricular tachycardia (SVT) minimum rate, supraventricular Ectopic (SVE) minimum rate and supraventricular ectopic (SVE) prematurity.

9. The method of claim 1 wherein establishing a connection further comprises mapping a memory area of each device to a storage area of the central server assigned to the patient, said memory area including the ECG data of the patient.

10. The method of claim 1 wherein establishing a connection comprises establishing a connection between a server and a sensor for transferring the ECG data from said sensor to said server.

11. The method of claim 1 wherein the data storage area on the central server includes a data storage area assigned to the patient, and wherein said storing comprises storing the ECG data at the data storage area assigned to the patient at the central server.

12. The method of claim 1, further comprising decompressing the ECG data and storing the decompressed ECG data at a data storage area of the central server.

13. The method of claim 1 wherein the ECG data includes patient demographics information.

14. The method of claim 1 wherein the ECG data is Holter data and wherein the report is a Holter analysis report.

15. The method of claim 1 wherein the analysis setup parameters include at least one of define calibration beat, define normal beat, create beat template, analyze paced beats only, ST analysis (inverted or uninverted) and QT analysis (inverted or uninverted).

16. The method of claim 1 wherein the analysis options include at least one of ST depression limit, ST elevation limit, minimum pause limit, tachycardia rate, bradycardia rate, supraventricular tachycardia (SVT) minimum rate, supraventricular Ectopic (SVE) minimum rate and supraventricular ectopic (SVE) prematurity.

17. The method of claim 16 wherein the analysis setup parameters include at least one of define calibration beat, define normal beat, create beat template, analyze paced beats only, ST analysis (inverted or uninverted) and QT analysis (inverted or uninverted).

18. A system for analyzing ECG data of a patient over a communication network, said system comprising:
a central server;
an interface for transferring first ECG data from a first source to the central server over the communication network and for transferring second ECG data from a second source to the central server over the communication network wherein the first source and the second source are remote from each other and remote from the central server, said second ECG data different from the first ECG data;
a storage area at the central server for storing the received first ECG data and the received second ECG data;
ECG data analysis software executed by the central server for analyzing the stored first ECG data and the stored second ECG data without downloading said stored first ECG data and the stored second ECG data to a computing device separate from the central server;
a user interface at the central server for providing various analysis options to a first user at first analysis site, said provided analysis options enabling the first user to interact with the stored first ECG data at the central server without downloading the first stored ECG data to the first user from the first analysis site, said first analysis site being remote with respect to the central server and the first and second sources;
wherein the first user interface receives first instructions from the first user at the first analysis site in response to the provided analysis options, wherein the received first instructions from the first user include first analysis setup parameters and first analysis options for configuring the ECG data analysis software on the central server;
said user interface at the central server for providing various analysis options to a second user at a second analysis site, said second user different from the first user, said provided analysis options enabling the second user to interact with the stored second ECG data at the central server without downloading the stored second ECG data to the user from the analysis site, said second analysis site being remote with respect to the central server, the first analysis site and the first and second sources;
wherein the second user interface receives second instructions from the second user at the second analysis site in response to the provided analysis options, wherein the received second instructions from the second user include second analysis setup parameters and second analysis options for configuring the ECG data analysis software on the central server;
wherein the second analysis setup parameters received from the second user are different from the first analysis setup parameters received from the first user and the second analysis options received from the second user are different from the first analysis options received from the first user; and a processor on the central server for executing the ECG data analysis software:
to analyze the stored first ECG data,
to generate a first report on the central server based on the received first analysis setup parameters and first analysis options, and
to notify a designated first computing device that is located remote from the central server that the first report has been generated and is available for access and review,
said user interface for transferring the first report from the central server to the first source; and
said processor on the central server for executing the ECG data analysis software:
to analyze the stored second ECG data,
to generate a second report on the central server based on the received second analysis setup parameters and second analysis options, and
to notify a designated second computing device that is located remote from the central server that the second report has been generated and is available for access and review,
said user interface for transferring the second report from the central server to the second source wherein the processor on the central server analyzes two different ECG data in two different ways as specified by two different users so that the first ECG data is analyzed according to the first analysis setup parameters and the first analysis options specified by the first user and so that the second ECG data is analyzed according to the second analysis setup parameters and the second analysis options specified by second first user.

19. The system of claim 18 wherein the sensed ECG data is transferred from the sensor via a port on a remote computer over the communication network to the central server so that the ECG data is stored on the central server and is not stored by the remote computer.

20. The system of claim 18 wherein the sensor includes at least one of the following interfaces: a USB interface and a PCMCIA flashcard interface.

21. The system of claim 18 wherein the second interface transfers the sensed ECG data from a computer over the communication network to the central server so that the ECG data is stored on the central server, said computer receiving the sensed ECG data from the sensor.

22. The system of claim 18 wherein the sensor is a Holter monitor.

23. The system of claim 18 wherein the second interface comprises a web page wherein the computer at the analysis site is configured with a web browser for the user to access the web page hosted by the central server wherein the web page is configured to map the sensor connecting to the computer at the analysis site via the first interface to a storage area of the central server assigned to the patient.

24. The system of claim 18 wherein the third interface includes an interface for uses by the user for registering the patient.

25. The system of claim 18 wherein the fourth interface comprises a web page wherein the computer at the analysis site is configured with the web browser for the user to access the web page hosted by the central server.

26. The system of claim 18 wherein the ECG data is Holter data and wherein the report is a Holter analysis report.

27. The system of claim 18 wherein the ECG data includes patient demographics information.

28. The system of claim 18 wherein the interface comprises a web page hosted by the central server.

29. The system of claim 18 wherein each source comprises a computer having access to the ECG data.

30. The system of claim 29 wherein each source comprises a sensor that senses the ECG data, said sensor storing the sensed ECG data in a storage area before transferring the sensed ECG data from the sensor to the central server and wherein the ECG data is transferred from the storage area to the central server without intermediate storage.

31. The system of claim 29 wherein the computer is configured with a web browser for a user to access the web page.

32. The system of claim 18 wherein the storage area comprises a particular storage area assigned to the patient for storing the ECG data.

33. The system of claim 18 wherein the processor decompresses the ECG data and analyzes the decompressed ECG using the ECG data analysis software on the central server to generate the report on the central server.

34. The system of claim 18 wherein the analysis setup parameters include at least one of define calibration beat, define normal beat, create beat template, analyze paced beats only, ST analysis (inverted or uninverted) and QT analysis (inverted or uninverted).

35. The system of claim 18 wherein the analysis options include at least one of ST depression limit, ST elevation limit, minimum pause limit, tachycardia rate, bradycardia rate, supraventricular tachycardia (SVT) minimum rate, supraventricular Ectopic (SVE) minimum rate and supraventricular ectopic (SVE) prematurity.

36. A system for analyzing ECG data of a patient over a communication network, said system comprising:
a central server;
an interface for transferring first ECG data from a first source to the central server over the communication network and for transferring second ECG data from a second source to the central server over the communication network wherein the first source and the second source are remote from each other and remote from the central server, said second ECG data different from the first ECG data;
a storage area at the central server for storing the received first ECG data and the received second ECG data;
ECG data analysis software executed by the central server for analyzing the stored first ECG data and the stored second ECG data without downloading said stored first ECG data and the stored second ECG data to a computing device separate from the central server;
a user interface at the central server for providing various analysis options to a first user at first analysis site, said provided analysis options enabling the first user to interact with the stored first ECG data at the central server without downloading the first stored ECG data to the first user from the first analysis site, said first analysis site being remote with respect to the central server and the first and second sources;
wherein the first user interface receives first instructions from the first user at the first analysis site in response to the provided analysis options, wherein the received first instructions from the first user include first analysis setup parameters and first analysis options for configuring the ECG data analysis software on the central server;
said user interface at the central server for providing various analysis options to a second user at a second analysis site, said second user different from the first user, said provided analysis options enabling the second user to interact with the stored second ECG data at the central server without downloading the stored second ECG data to the user from the analysis site, said second analysis site being remote with respect to the central server, the first analysis site and the first and second sources;

wherein the second user interface receives second instructions from the second user at the second analysis site in response to the provided analysis options, wherein the received second instructions from the second user include second analysis setup parameters and second analysis options for configuring the ECG data analysis software on the central server;

wherein the second analysis setup parameters received from the second user are different from the first analysis setup parameters received from the first user and the second analysis options received from the second user are different from the first analysis options received from the first user; and a processor on the central server for executing the ECG data analysis software:
- to analyze the stored first ECG data and to analyze the stored second ECG data,
- to generate a first report on the central server based on the received first analysis setup parameters and first analysis options and to generate a second report on the central server based on the received second analysis setup parameters and second analysis options, and
- to notify a designated first computing device that is located remote from the central server that the first report has been generated and is available for access and review and to notify a designated second computing device that is located remote from the central server that the second report has been generated and is available for access and review,
- said user interface for transferring the first report from the central server to the first source and said user interface for transferring the second report from the central server to the second source, wherein the processor of the central server analyzes two different ECG data in two different ways as specified by two different users so that the first ECG data is analyzed according to the first analysis setup parameters and the first analysis options specified by the first user and so that the second ECG data is analyzed according to the second analysis setup parameters and the second analysis options specified by second first user.

37. The system of claim 36 wherein the first analysis setup parameters include at least one of define calibration beat, define normal beat, create beat template, analyze paced beats only, ST analysis (inverted or uninverted) and QT analysis (inverted or uninverted) and wherein the second analysis setup parameters include at least one of define calibration beat, define normal beat, create beat template, analyze paced beats only, ST analysis (inverted or uninverted) and QT analysis (inverted or uninverted).

38. The system of claim 37 wherein the first analysis options include at least one of ST depression limit, ST elevation limit, minimum pause limit, tachycardia rate, bradycardia rate, supraventricular tachycardia (SVT) minimum rate, supraventricular Ectopic (SVE) minimum rate and supraventricular ectopic (SVE) prematurity and wherein the second analysis options include at least one of ST depression limit, ST elevation limit, minimum pause limit, tachycardia rate, bradycardia rate, supraventricular tachycardia (SVT) minimum rate, supraventricular Ectopic (SVE) minimum rate and supraventricular ectopic (SVE) prematurity.

39. The system of claim 38 wherein the first analysis setup parameters include at least one of define calibration beat, define normal beat, create beat template, analyze paced beats only, ST analysis (inverted or uninverted) and QT analysis (inverted or uninverted) and wherein the second analysis setup parameters include at least one of define calibration beat, define normal beat, create beat template, analyze paced beats only, ST analysis (inverted or uninverted) and QT analysis (inverted or uninverted).

* * * * *